(12) United States Patent
Milbert et al.

(10) Patent No.: US 12,070,326 B2
(45) Date of Patent: *Aug. 27, 2024

(54) SYSTEMS AND METHODS FOR AUTOMATED STRESS MONITORING AND INTERVENTION

(71) Applicant: NightWare, Inc., Minneapolis, MN (US)

(72) Inventors: Randy Milbert, Edina, MN (US); Tyler Skluzacek, Chicago, IL (US)

(73) Assignee: NIGHTWARE, INC., Minneapolis, MN (US)

(*) Notice: Subject to any disclaimer, the term of this patent is extended or adjusted under 35 U.S.C. 154(b) by 99 days.

This patent is subject to a terminal disclaimer.

(21) Appl. No.: 17/689,262

(22) Filed: Mar. 8, 2022

(65) Prior Publication Data

US 2022/0346704 A1 Nov. 3, 2022

Related U.S. Application Data

(63) Continuation of application No. 16/405,193, filed on May 7, 2019, now Pat. No. 11,284,834.

(Continued)

(51) Int. Cl.
*A61B 5/00* (2006.01)
*A61B 5/0205* (2006.01)
(Continued)

(52) U.S. Cl.
CPC .......... *A61B 5/4815* (2013.01); *A61B 5/0205* (2013.01); *A61B 5/165* (2013.01);
(Continued)

(58) Field of Classification Search
CPC ..... A61B 5/4815; A61B 5/0205; A61B 5/165; A61B 5/7282; A61B 5/746; A61B 5/0002;
(Continued)

(56) References Cited

U.S. PATENT DOCUMENTS 10,252,058 B1 * 4/2019 Fuerst ................ A61N 1/36014
10,765,831 B1    9/2020 Skluzacek
(Continued)

FOREIGN PATENT DOCUMENTS

WO    WO-2010107788 A2    9/2010

OTHER PUBLICATIONS

"Tom M. Mitchell, the Discipline of Machine Learning, Jul. 2006, CMU-ML-06-108" (Year: 2006).*

(Continued)

*Primary Examiner* — Joseph M Dietrich
*Assistant Examiner* — Michael T. Holtzclaw
(74) *Attorney, Agent, or Firm* — SCHWEGMAN LUNDBERG & WOESSNER, P.A.

(57) ABSTRACT

Systems and methods for detection and/or intervention of stress episodes such as nightmares during sleep activity or flashbacks or anxiety attacks during waking or sleep activity. In some embodiments, sensors, such as gyroscopes, accelerometers, heart rate sensors, and/or other sensors, may be used for monitoring stress indicators indicative of a user's stress level. The sensed stress indicators may be used to calculate a stress level. If the stress level meets or exceeds a stress level threshold, haptic, audio, visual, and/or other feedback or alerts may be used to draw a user's attention and thus interrupt the stress episode.

19 Claims, 40 Drawing Sheets

Related U.S. Application Data

(60) Provisional application No. 62/667,761, filed on May 7, 2018.

(51) Int. Cl.
  *A61B 5/11* (2006.01)
  *A61B 5/16* (2006.01)
  *A61M 21/00* (2006.01)

(52) U.S. Cl.
  CPC ............ *A61B 5/7282* (2013.01); *A61B 5/746* (2013.01); *A61B 5/0002* (2013.01); *A61B 5/11* (2013.01); *A61B 5/6802* (2013.01); *A61M 2021/0022* (2013.01); *A61M 2021/0027* (2013.01); *A61M 2021/0044* (2013.01)

(58) Field of Classification Search
  CPC .................. A61B 5/11; A61B 5/6802; A61M 2021/0022; A61M 2021/0027; A61M 2021/0044
  See application file for complete search history.

(56) References Cited

U.S. PATENT DOCUMENTS

| | | | |
|---|---|---|---|
| 11,284,834 | B1 | 3/2022 | Milbert et al. |
| 11,471,644 | B2 | 10/2022 | Skluzacek |
| 2005/0154264 | A1 | 7/2005 | Lecompte et al. |
| 2011/0245633 | A1* | 10/2011 | Goldberg ............... A61B 5/165 600/323 |
| 2014/0245784 | A1 | 9/2014 | Proud et al. |
| 2015/0031964 | A1 | 1/2015 | Bly et al. |
| 2015/0087894 | A1 | 3/2015 | Rink et al. |
| 2015/0169844 | A1 | 6/2015 | Munafo et al. |
| 2016/0296157 | A1 | 10/2016 | Girouard |
| 2017/0071551 | A1 | 3/2017 | Jain et al. |
| 2017/0209053 | A1 | 7/2017 | Pantelopoulos et al. |
| 2018/0116607 | A1 | 5/2018 | Yu et al. |
| 2019/0357834 | A1* | 11/2019 | Aarts .................. A61B 5/7246 |
| 2020/0376231 | A1 | 12/2020 | Skluzacek |
| 2021/0068736 | A1* | 3/2021 | Grahm .................. G16H 40/63 |
| 2023/0038328 | A1 | 2/2023 | Skluzacek |

OTHER PUBLICATIONS

"U.S. Appl. No. 15/713,313, Final Office Action mailed Feb. 6, 2020", 9 pgs.

"U.S. Appl. No. 15/713,313, Non Final Office Action mailed Aug. 2, 2019", 8 pgs.

"U.S. Appl. No. 15/713,313, Notice of Allowance mailed May 6, 2020", 7 pgs.

"U.S. Appl. No. 15/713,313, Response filed Apr. 6, 2020 to Final Office Action mailed Feb. 6, 2020", 8 pgs.

"U.S. Appl. No. 15/713,313, Response Filed Nov. 4, 2019 to Non Final Office Action mailed Aug. 2, 2019", 9 pgs.

"U.S. Appl. No. 16/405,193, Final Office Action mailed Feb. 12, 2021".

"U.S. Appl. No. 16/405,193, Non Final Office Action mailed Jul. 6, 2021", 20 pgs.

"U.S. Appl. No. 16/405,193, Non Final Office Action mailed Oct. 22, 2020".

"U.S. Appl. No. 16/405,193, Notice of Allowability mailed Dec. 9, 2021", 2 pgs.

"U.S. Appl. No. 16/405,193, Notice of Allowance mailed Nov. 19, 2021", 11 pgs.

"U.S. Appl. No. 16/405,193, Response filed Jan. 19, 2021 to Non Final Office Action mailed Oct. 22, 2020".

"U.S. Appl. No. 16/405,193, Response filed Jun. 11, 2021 to Final Office Action mailed Feb. 12, 2021", 16 pages.

"U.S. Appl. No. 16/405,193, Response filed Sep. 24, 2021 to Non Final Office Action mailed Jul. 6, 2021", 12 pages.

"U.S. Appl. No. 16/994,818, Non Final Office Action mailed Sep. 29, 2021", 10 pgs.

"U.S. Appl. No. 16/994,818, Notice of Allowance mailed Jun. 15, 2022", 7 pgs.

"U.S. Appl. No. 16/994,818, Response filed Feb. 22, 2022 to Non Final Office Action mailed Sep. 29, 2021", 10 pgs.

"U.S. Appl. No. 17/948,561, Preliminary Amendment filed Oct. 20, 2022", 8 pgs.

"U.S. Appl. No. 17/948,561, Non Final Office Action mailed Mar. 2, 2023", 4 pgs.

"U.S. Appl. No. 17/948,561, Response filed Mar. 3, 2023 to Non Final Office Action mailed Mar. 2, 2023", 6 pgs.

"U.S. Appl. No. 17/948,561, Notice of Allowance mailed Mar. 14, 2023", 7 pgs.

\* cited by examiner

/dashboard 300

/log 302

Fig. 4

| /api/event | 400 |
|---|---|
| Events : List<Event><br>User Key : String | |

| /api/export | 402 |
|---|---|
| Type : String | |

| /api/release | 404 |
|---|---|

| /api/sample | 406 |
|---|---|
| Aggregate : Boolean<br>End Time : Long<br>Start Time : Long<br>User Id : String | |

| /api/summary | 408 |
|---|---|

| /api/threshold | 410 |
|---|---|

| /api/user | 412 |
|---|---|
| User Key : String | |

Fig. 5

Event 500

Description : String
Error : Boolean
Id : Long
Time : Long
User Id : String

Sample 502

Accelerometer : Float
Gyroscope : Float
Heart Rate : Float
Intervention : Integer
Id : Long
Stress : Float
Time : Long
User Id : String

User 504

Accepted Release Date : Date
Created Date : Date
Email : String
Key : String
Level : Integer
Name : String
Nickname : String
Patients : List<User>

| Name | Start | End | Hours | Interventions | Minimum Stress | Average Stress | Maximum Stress |
|---|---|---|---|---|---|---|---|
| | 12:11 AM | 8:31 AM | 8 | 1 | 33 | 36 | 51 |
| | 10:09 PM | 6:15 AM | 8 | 12 | 34 | 42 | 56 |
| | 12:00 PM | 11:59 AM | 23 | 4 | 36 | 42 | 63 |
| | 10:44 PM | 6:50 AM | 8 | 12 | 40 | 45 | 56 |
| | 10:59 PM | 3:44 AM | 4 | 12 | 34 | 39 | 71 |
| | 10:33 PM | 6:06 AM | 7 | 165 | 40 | 46 | 52 |
| | 10:28 PM | 6:59 AM | 8 | 6 | 30 | 37 | 69 |
| | 11:04 PM | 5:45 AM | 6 | 1 | 34 | 43 | 60 |
| | 9:39 PM | 4:12 AM | 6 | 7 | 27 | 37 | 64 |
| | 1:25 AM | 8:40 AM | 7 | 6 | 36 | 41 | 57 |
| | 9:19 PM | 3:58 AM | 6 | 6 | 32 | 37 | 56 |
| | 9:19 PM | 10:11 PM | 0 | 0 | 36 | 39 | 54 |
| | 10:25 PM | 6:50 AM | 8 | 2 | 32 | 37 | 55 |
| | 9:20 PM | 7:42 AM | 10 | 15 | 36 | 43 | 69 |
| | 7:43 PM | 11:48 PM | 4 | 22 | 38 | 43 | 65 |
| | 2:41 AM | 7:32 AM | 4 | 4 | 34 | 36 | 58 |
| | 12:37 AM | 10:04 AM | 9 | 1 | 34 | 41 | 62 |
| | 10:10 PM | 2:32 AM | 4 | 6 | 29 | 36 | 59 |

For details, see the NightWare dashboard. 3516

Fig. 36

SYSTEMS AND METHODS FOR AUTOMATED STRESS MONITORING AND INTERVENTION

CROSS-REFERENCE TO RELATED APPLICATIONS

This application is a continuation of U.S. application Ser. No. 16/405,193, entitled "Systems and Methods for Automated Stress Monitoring and Intervention," filed May 7, 2019, which claims priority to U.S. Provisional Application No. 62/667,761, entitled "Traumatic Nightmare Detection and Intervention," filed May 7, 2018, each of which is hereby incorporated by reference herein in its entirety. This application additionally relates to U.S. Provisional Application No. 62/389,908, filed Sep. 23, 2016, and U.S. Non-Provisional application Ser. No. 15/713,313, entitled "Traumatic Nightmare Detection and Intervention," filed Sep. 22, 2017, each of which is also hereby incorporated by reference herein in its entirety.

FIELD OF THE INVENTION

The present disclosure relates to systems and methods for determining an individual's stress level in real-time or near real-time. In particular, the present disclosure relates to systems and methods for determining whether an individual is experiencing a nightmare, anxiety attack, flashback, or other stress episode. More particularly, the present disclosure relates to systems and methods for interrupting a nightmare, anxiety attack, flashback, or other stress episode.

BACKGROUND OF THE INVENTION

The background description provided herein is for the purpose of generally presenting the context of the disclosure. Work of the presently named inventor, to the extent it is described in this background section, as well as aspects of the description that may not otherwise qualify as prior art at the time of filing, are neither expressly nor impliedly admitted as prior art against the present disclosure.

Nightmares are a condition that affects a substantial number of persons. Individuals who suffer from post-traumatic stress disorder (PTSD) may experience particularly traumatic nightmares. Military veterans, first responders, and crime victims may be particularly afflicted with nightmares because of traumatic experiences that have created PTSD. Traumatic nightmares can be so impactful that restful sleep is negatively affected, and fragmented, possibly at times rendering people unable to function normally in their daily lives. Such individuals may additionally or alternatively suffer from anxiety attacks, flashback episodes, and/or other traumatic or stressful events. Problems associated with PTSD may be particularly acute in the community of military veterans who have returned from combat operations. Moreover, societal stigma, self-esteem, and/or other concerns may deter military veterans and others from seeking clinical treatment for nightmares, anxiety, flashbacks, and/or similar conditions.

Conventional approaches to treating traumatic nightmares typically involve complex solutions in clinical settings using prolonged exposure or similar treatments. Drawbacks to such conventional approaches include high cost, complexity, side effects, and/or ineffectiveness.

Thus, there is a need in the art for systems and methods for addressing, and in particular interrupting, preventing, or stopping, stress episodes. In particular, there is a need in the art for interrupting, preventing, or stopping nightmares, anxiety attacks, and flashbacks. More particularly, there is a need in the art for systems and methods for interrupting, preventing, or stopping such stress episodes using a wearable device or other user device.

BRIEF SUMMARY OF THE INVENTION

The following presents a simplified summary of one or more embodiments of the present disclosure in order to provide a basic understanding of such embodiments. This summary is not an extensive overview of all contemplated embodiments, and is intended to neither identify key or critical elements of all embodiments, nor delineate the scope of any or all embodiments.

The present disclosure, in one or more embodiments, relates to a method for monitoring a user's stress level and for interrupting a stress episode. The method may include determining a stress level threshold for the user, the stress level threshold indicating a stress level at which the user is likely experiencing a stress episode. The method may additionally include receiving a sensor reading from a sensor configured to sense a stress indicator of the user. The method may include, based on the sensor reading, calculating a stress level for the user and comparing the calculated stress level to the stress level threshold. If the stress level exceeds the stress level threshold, the method may include initiating an intervention protocol at a user device to alert the user and interrupt the stress episode, the intervention protocol including haptic, audio, and/or visual feedback at the user device. In some embodiments, receiving a sensor reading may include receiving a sensor reading for each of a plurality of intervals over a period of time, and calculating a stress level may include calculating a stress level for each interval. The method may include calculating an average stress level for the period of time. In some embodiments, the period of time may be one minute and each interval may be one second. In some embodiments, stress indicators may be received from a plurality of sensors, each sensor configured to sense a stress indicator of the user. Moreover, calculating a stress level may include mathematically combining the sensor readings of the plurality of sensors. In some embodiments, the stress level threshold may be based on a specified percentile of historical calculated stress levels for the user. The sensor may include a gyroscope, accelerometer, and/or heart rate monitor. The user device may be a wearable device and the sensor may be arranged on the user device. In some embodiments, the sensor reading may include coordinate data, and the method may include calculating a magnitude for the sensor reading. The method may additionally include determining an amount of time since a most recent intervention protocol and comparing the amount of time since a most recent intervention protocol to a stored minimum frequency. Initiating an intervention protocol to interrupt the stress episode may be performed only if the amount of time since a most recent intervention protocol meets or exceeds the minimum frequency.

The present disclosure, in one or more embodiments, additionally relates to a user device configured for monitoring a user's stress level and for interrupting a stress episode. The device may include a sensor configured to sense a stress indicator of the user, the sensor including at gyroscope, accelerometer, and/or heart rate monitor. The device may additionally include a feedback device configured to alert the user of a stress episode and thereby interrupt the stress episode. The feedback device may include a haptic, video, and/or audio feedback device. The user device may additionally include a processor configured for instructing the sensor to begin monitoring the stress indicator, receiving stress indicator data from the sensor and, using the stress indicator data, calculating a stress level of the user. The processor may further be configured for determining whether the user is experiencing a stress episode based on the calculated stress level and, where it is determined that the user is experiencing a stress episode, causing the feedback device to alert the user. The device may additionally include a database storing, on non-transitory computer readable storage media, monitoring data comprising sensed stress indicator data. The user device may be a wearable device in some embodiments. In other embodiments, the user device may be a smartphone. Determining whether the user is experiencing a stress episode may include comparing the calculated stress level to a stored stress level threshold. The threshold may be a learned threshold, and the processor may further be configured for establishing a learned threshold based on received stress indicator data. In some embodiments, the stress level threshold may be based on a specified percentile of a plurality of calculated stress levels of the user over a period of time.

The present disclosure, in one or more embodiments, additionally relates to a non-transitory computer readable storage medium encoded with computer executable instructions for monitoring a user's stress level and for interrupting a stress episode. In particular, the instructions may be configured for determining a stress level threshold for the user, the stress level threshold indicating a stress level at which the user is likely experiencing a stress episode. The instructions may further be configured for receiving a sensor reading from a sensor configured to sense a stress indicator of the user. The instructions may further be configured for calculating a stress level for the user based on the sensor reading. The instructions may further be configured for comparing the calculated stress level to the stress level threshold and, where the stress level exceeds the stress level threshold, initiating an intervention protocol at a user device to alert the user and interrupt the stress episode, the intervention protocol including haptic, audio, and/or visual feedback at the user device. In some embodiments, receiving a sensor reading may include receiving a sensor reading for each of a plurality of intervals over a period of time and calculating a stress level may include calculating a stress level for each interval. The computer executable instructions may further be configured for determining an amount of time since a most recent intervention protocol and comparing the amount of time since a most recent intervention protocol to a stored minimum frequency. In some embodiments, initiating an intervention protocol to interrupt the stress episode may be performed only if the amount of time since a most recent intervention protocol meets or exceeds the minimum frequency.

While multiple embodiments are disclosed, still other embodiments of the present disclosure will become apparent to those skilled in the art from the following detailed description, which shows and describes illustrative embodiments of the invention. As will be realized, the various embodiments of the present disclosure are capable of modifications in various obvious aspects, all without departing from the spirit and scope of the present disclosure. Accordingly, the drawings and detailed description are to be regarded as illustrative in nature and not restrictive.

BRIEF DESCRIPTION OF THE DRAWINGS

While the specification concludes with claims particularly pointing out and distinctly claiming the subject matter that is regarded as forming the various embodiments of the present disclosure, it is believed that the invention will be better understood from the following description taken in conjunction with the accompanying Figures, in which:

FIG. 4 is a listing of data pages that may be provided via a user interface of the present disclosure, according to one or more embodiments.

FIG. 5 is a listing of data services that may be performable by a system of the present disclosure, according to one or more embodiments.

FIG. 6 is a listing of data models that may be compiled by a system of the present disclosure, according to one or more embodiments.

FIG. 35 is a screenshot of a dashboard page of a user interface of the present disclosure showing a user's logged events for a day, according to one or more embodiments.

FIG. 36 is a screenshot of an email containing a summary of user monitoring data for a day, according to one or more embodiments.

DETAILED DESCRIPTION

The present disclosure relates to systems and methods for detection and/or intervention of stress episodes. In particular, the present disclosure relates to systems and methods for detection and/or intervention of stress episodes such as nightmares during sleep activity or flashbacks or anxiety attacks during waking or sleep activity. In some embodiments, sensors, such as gyroscopes, accelerometers, heart rate sensors, and/or other sensors, may be used for monitoring stress indicators indicative of a user's stress level. A stress level may be calculated from the sensed stress indicator data. If the calculated stress level meets or exceeds a stored stress level threshold, it may be determined that the user is likely experiencing a stress episode, and haptic audio, visual, and/or other feedback or alerts may be used to interrupt the stress episode by drawing the user's attention. Where the user is sleeping and the stress episode is likely a nightmare, the alert may be configured to wake the user, to bring the user out of a rapid eye movement (REM) cycle, or otherwise to disrupt or stop the nightmare and thereby reduce the user's stress level. Embodiments of the present disclosure may operate using one or more wearable devices, such as a smartwatch, for sensing stress indicator data and/or for providing haptic or other feedback to alert the user. A software application providing a user interface may be provided via the wearable device and/or via another user device such as a smartphone, tablet, or computer. The user interface may allow the user to control monitoring operations, control alert and stress settings, and/or view historical monitoring and stress events. Additionally, in some embodiments, a user interface may provide access to additional users, such as family members, caretakers, or medical professions.

Figure 1:
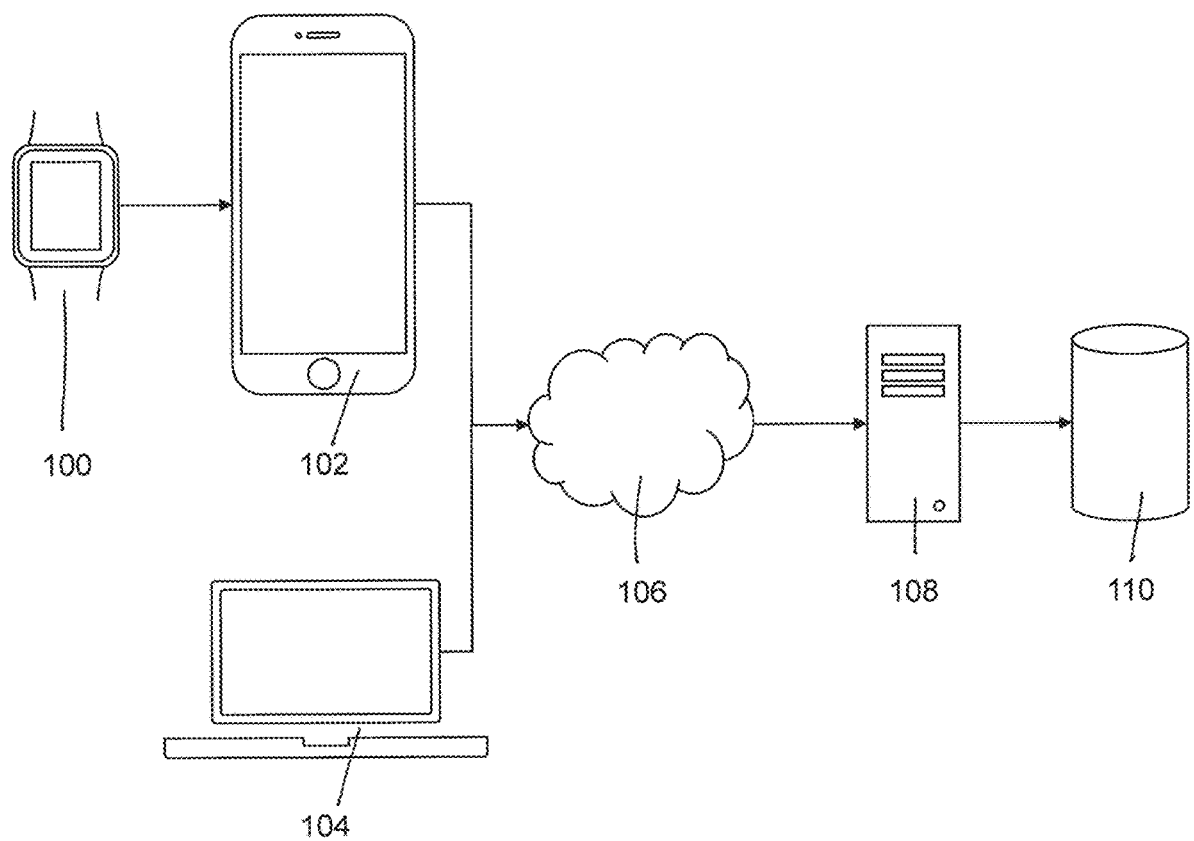
FIG. 1 is a diagram of a stress detection and intervention system of the present disclosure, according to one or more embodiments.

Turning now to FIG. 1, a system of the present disclosure is shown, according to one or more embodiments. The system may generally include a user device portion, which may include one or more user device components, in electronic communication with a server 108 and database 110. The user device portion of the system may include one or more user devices, which may be or include a wearable device 100, a personal device 102, and/or a computing device or processor 104. The user device portion of the system may communicate with the server 108 and database 110 over an electronic communication network 106. The network 106 may include one or more wired or wireless networks allowing for electronic communication between the various components of the system. In some embodiments, the network 106 may include a local area network (LAN), a wide area network (WAN), hotspot, a global communications network, such as the Internet, and/or other suitable network environments. It is to be appreciated that in some embodiments, the system or components thereof may be components of a single user device (such a wearable device 100 or personal device 102). In particular, a user device may include a processor and/or database. Thus, functionality of the system may be provided by a self-contained device, and in some embodiments, the system may operate without a need for network connectivity.

The wearable device 100 may be configured for sensing one or more stress indicators of the user and/or for providing haptic, audio, visual, or other alerts to intervene in a stress episode. The wearable device 100 may be or include a smartwatch, fitness tracker, heart rate monitor, and/or other wearable device. The device 100 may have one or more sensors, such as but not limited to a gyroscope, accelerometer, heart rate monitor, galvanic skin response sensor, oximetry sensor, microphone, or temperature sensor. The sensor(s) may be configured to sense stress indicators, or indications that the user may be experiencing an elevated stress level. The wearable device 100 may further be configured to provide haptic feedback, such as vibration, in some embodiments. In some embodiments, the device 100 may additionally be configured to provide visual and/or audio feedback, having speakers, lights, and/or a screen or monitor.

In addition to, or alternative to, the wearable device 100, the system may include a personal device 102. The user device may be or include a smartphone, tablet, desktop computer, laptop computer, or other computing device. In some embodiments, the user device may be configured for sensing stress indicators, in addition or alternative to, stress indicators sensed by the wearable device 100. For example, the personal device 102 may have one or more of a gyroscope, accelerometer, heart rate monitor, galvanic skin response sensor, oximetry sensor, microphone, or temperature sensor. In some embodiments, the personal device 102 may be configured to provide haptic, audio, and/or visual feedback. In this way, the user may be alerted via the user device in addition or alternative to an alert via the wearable device 100. For example, the personal device 102 may be configured to provide haptic feedback, such as vibration, in some embodiments. In some embodiments, the personal device 102 may additionally be configured to provide visual and/or audio feedback, having speakers, lights, and/or a screen or monitor.

The wearable device 100 and/or personal device 102 may be encoded with computer executable instructions for a software application (also referred to herein as an "app"). The software application may provide a user interface for a user to interact with the system. Through the user interface, the user may have the ability to control settings and options related to stress monitoring and intervention protocols, control (i.e., start and stop) stress monitoring, view historical stress data, and send or share historical stress data. The user interface is described in more detail with respect to FIGS. 22-39.

Figure 2:
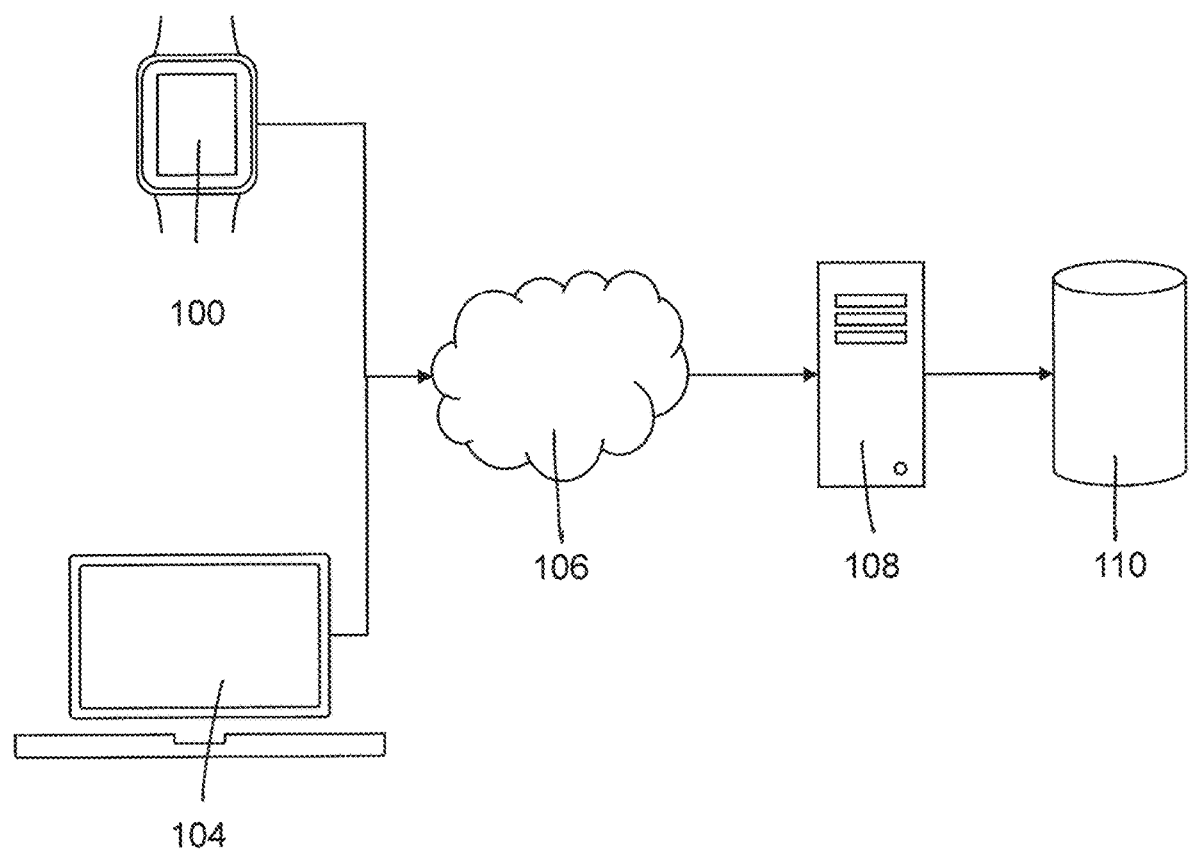
FIG. 2 is a diagram of a stress detection and intervention system of the present disclosure, according to one or more embodiments.

It is to be appreciated that, while in some embodiments the system may include both a wearable device 100 and a personal device 102, in other embodiments, the system may include either the user device or the wearable device. For example, FIG. 2 shows an embodiment of a system that excludes a user device. In this way, the wearable device may provide the user interface and software application functionality for the user.

The computing device 104 may be or include one or more processors comprising hardware and/or software for carrying out operations described herein. For example, the computing device 104 may be configured to compile data, perform calculations, execute and manage decision logic, and/or perform other suitable operations. In some embodiments, the computing device 104 may be, or may be incorporated into, the user device or the wearable device. In other embodiments, the computing device 104 may be or include a separate computer or processor in communication with the personal device 102 and/or wearable device 100. In some embodiments, the computing device 104 may include a stress threshold module, a monitoring module, and an intervention module.

The stress threshold module may include hardware and/or software for determining one or more stress thresholds. A stress threshold may be a value or limit indicative of high or relatively high stress and against which a stress level or stress indicator may be compared. In particular, a stress threshold may be a level or limit indicating that a user may be experiencing a traumatic nightmare or another stress episode. A stress threshold may be a stress indicator threshold against which sensor data may be directly compared to determine whether a user may be experiencing a stress episode. Additionally or alternatively, a stress threshold may be a stress level threshold against which a calculated or determined stress level may be compared to determine whether a user may be experiencing a stress episode.

In some embodiments, the stress threshold module may be configured to analyze stress data, such as historical stress data, to determine a suitable stress threshold, such as a learned stress threshold. For example, the stress threshold module may query the database 110 for the user's most recent 1,000 recorded stress levels and/or stress indicators, or another suitable number, to determine a suitable stress threshold. The stress threshold for a particular level or indicator may be determined to be a value representative of the $75^{th}$, $85^{th}$, $90^{th}$, $95^{th}$, or $99^{th}$ percentile, or other suitable percentile, of the historical data. Based on the user's historical data, such high percentile values may indicate the user's stress levels while the user experiences relatively high stress. In this way, it is to be appreciated that individuals may experience stress differently and may experience different heart rates and/or other symptoms indicative of relatively high stress. Moreover, different individuals may have different tolerances for stress. Thus, the user's own historical stress data may be used to determine a suitable stress threshold for that user. In other embodiments, the historical value may be evaluated differently to determine or calculate a suitable value representative of relatively high stress levels for the user. In still other embodiments, a stress threshold may be determined as a default value. For example, where the user does not have enough historical data to determine a custom stress threshold tailored for the user, a default stress threshold may be set. In some embodiments, a user may have the option to change or modify stress thresholds. In different embodiments, the stress threshold module may include only hardware, only software, or a combination of hardware and software. In some embodiments, the stress threshold module may be or include computer-executable instructions encoded on a non-transitory computer readable storage medium.

The monitoring module may include hardware and/or software for monitoring one or more user stress indicators. In particular, the monitoring module may be configured to initiate monitoring by triggering one or more sensors to collect data and/or by causing the database 110 to begin storing sensed data. In some embodiments, the monitoring module may detect when monitoring should begin. For example, the monitoring module may evaluate sensor data to estimate when a user may be sleeping, and may initiate monitoring upon such estimation. In other embodiments, the user may indicate via a user interface when monitoring should be initiated. In still other embodiments, the monitoring module may monitor data continuously, intermittently, at intervals, on demand, or randomly. The monitoring module may further be configured to evaluate sensed data during monitoring. In particular, the monitoring module may be configured for determining or calculating a stress level based on the sensed data. As described in more detail below, the monitoring module may perform one or more calculations using sensed data to determine a numerical stress level. The monitoring module may determine or calculate a stress level continuously, intermittently, at intervals, on demand, or randomly. In some embodiments, the monitoring module may determine or calculate multiple stress levels. In different embodiments, the monitoring module may include only hardware, only software, or a combination of hardware and software. In some embodiments, the monitoring module may be or include computer-executable instructions encoded on a non-transitory computer readable storage medium.

The intervention module may include hardware and/or software for determining whether a user may be experiencing a stress episode and further for determining whether to intervene. In particular, the intervention module may be configured to compare stress levels and/or sensed stress indicators to one or more stress thresholds. Such comparisons may be made continuously (e.g., for each sensed data point or each determined stress level), intermittently, at intervals, randomly, or on demand. If it is determined that a stress level or indicator exceeds the applicable threshold (or in some embodiments, if the stress level or indicator meets the applicable threshold), the intervention module may determine whether an intervention protocol should be initiated to intervene in an attempt to lower the user's stress. To determine whether to intervene, the intervention module may evaluate a length of time since a most recent protocol was initiated or completed. An intervention frequency may determine a minimum interval between consecutive intervention protocols. For example, an intervention frequency may indicate that if an intervention protocol was initiated (or completed) within the past 15, 30, 45, or 60 seconds, or the past 1, 2, 3, 4, or 5 minutes, the user is likely aware of the particular episode and thus a next intervention module should not be initiated yet. The intervention module may compare a time t since the most recent intervention protocol to the intervention frequency to determine whether an intervention protocol should be initiated.

An intervention protocol may include haptic feedback, such as vibration, pulsing, temperature change, or other haptic feedback of a wearable device or other user device. Additionally or alternatively, an intervention protocol may include audio feedback, such as a tone or series of tones, a song, or another suitable audio feedback. Additionally or alternatively, an intervention protocol may include visual feedback, which may include steady or flashing lights, images or colors appearing on a user device screen, or other suitable visual feedback. In some embodiments, the intervention module may determine a suitable intervention level. For example, there may be different protocols for low, moderate, and high intervention levels. Selection of an appropriate intervention level may be based upon how high the user's stress levels or indicators are, how long the stress levels or indicators have been elevated, and/or on whether previous alerts have failed to lower the user's stress levels/indicators.

In different embodiments, the stress threshold module may include only hardware, only software, or a combination of hardware and software. In some embodiments, the intervention module may be or include computer-executable instructions encoded on a non-transitory computer readable storage medium.

Figure 4:
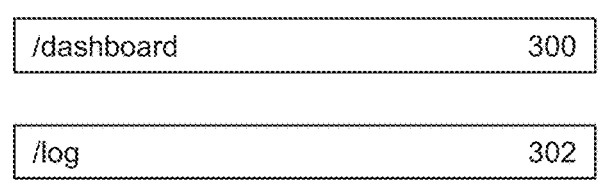

In some embodiments, the computing device 104 may be encoded with computer executable instructions for providing one or more data pages via the user interface. FIG. 4 is a list of some data pages the computing device 104 may be configured to provide or display. The dashboard page 300 may enable a user to view historic sensor values (or stress indicator values), stress levels, alerts, and/or other data related to the user's stress monitoring and intervention (see FIGS. 28 to 34). The log page 302 may enable a user to view events that have occurred such as a "starting monitoring" event, a "stopping monitoring" event, error events, alert or intervention events, and/or other events (see FIG. 35). Other data pages may be provided as well.

In some embodiments, the computing device 104 may be encoded with computer executable instructions for providing one or more data services or for performing one or more operations. FIG. 5 provides some examples of data services or operations that may be performed by the computing device 104. For example, an event service 400 may facilitate recording and retrieving events. When recording an event, the computing device 104 may accept an event list and a user key. An export service 402 may support exporting data from the database 110, such as event data, sample data, and/or user data. The computing device 104 may accept an entity type when exporting entities. A release service 404 may support determining whether a user has accepted a liability release and recording when the user does so. A sample service 406 may support recording and retrieving samples. A sample may be or include sensor data received from one or more sensors during a monitoring session. For example, a sample may be or include an accelerometer reading, a gyroscope reading, and a heart rate reading taken during a particular point in time. When retrieving samples, the computing device 104 may accept an aggregate value, end time, start time, and/or user identifier. A summary service 408 may support sending a daily, or other suitable time interval, summary via an email, text message, push notification, popup display, or other suitable type of communication. A threshold service 410 may support retrieving a user's stress threshold, which may be a learned or determined threshold based on historical stress indicator data. A user service 412 may facilitate user login into the user interface. The computing device 104 may accept a user key argument for the user service 412. Other services may be provided as well.

In some embodiments, the computing device 104 may be encoded with computer executable instructions for constructing or providing one or more data models. FIG. 6 lists some examples of data models that may be constructed or built by the computing device 104, and/or which may be stored in the database 110. An event model 500 may include data relating to one or more of a description, error value, identifier, time, and user identifier. A sample model 502 may include data relating to one or more of an accelerometer, gyroscope, heart rate, other stress indicator, intervention, identifier, stress, time, and user identifier values. A user model 504 may include data relating to one or more of an accepted release date, created date, email, key, level, name, nickname, and patient list values. Other models may be provided as well.

The database 110 may be or include one or more data storage devices storing data on non-transferrable computer readable storage media. The database 110 may include local storage devices, remote storage devices, or a combination thereof. That database 110 may store data such as, but not limited to, user data, threshold data, sensor data, stress level data, and alert data. User data may include identifying data, login data, personal data, medical data, and/or other data related to a particular user. Threshold data may include data related to one or more stress thresholds. For example, threshold data may include one or more particular stress threshold for a stress level or stress indicator, as designated by default, determined by a user, or calculated based on historical stress data. Sensor data may include information historically collected from one or more sensors, such as one or more gyroscopes, accelerometers, heart rate monitors, and/or other sensors. Historical sensor data may be maintained in the database for a number of days, weeks, months, years, indefinitely, until space is needed, or until a user identifies the historical data for removal. Stress level data may include historically calculated or determined stress levels for a user. Historical stress level data may be maintained in the database for a number of days, weeks, months, years, indefinitely, until space is needed, or until a user identifies the historical data for removal. Alert data may include settings related to one or more alerts, such as type of alert, alert length, and minimum frequency of alert. Alert data may additionally include historical alert data. Historical alert data may be maintained in the database for a number of days, weeks, months, years, indefinitely, until space is needed, or until a user identifies the historical data for removal. In some embodiments, the database 110 may be accessible by a user through the server 108. The server 108 may include one or more servers, each of which may be local or remote to the user and/or local or remote to the database 110. Additionally or alternatively, as described above, the database 110 may be or include a component of a user device, such as a wearable device 100 and/or a personal device 102.

It is to be appreciated that a system of the present disclosure may include additional or alternative components in some embodiments. For example, in addition or alternative to any of the components discussed above with respect to FIGS. 1 and 2, a system of the present disclosure may include any combination of the components discussed below with respect to FIG. 40 and/or any other suitable components.

Figure 3:
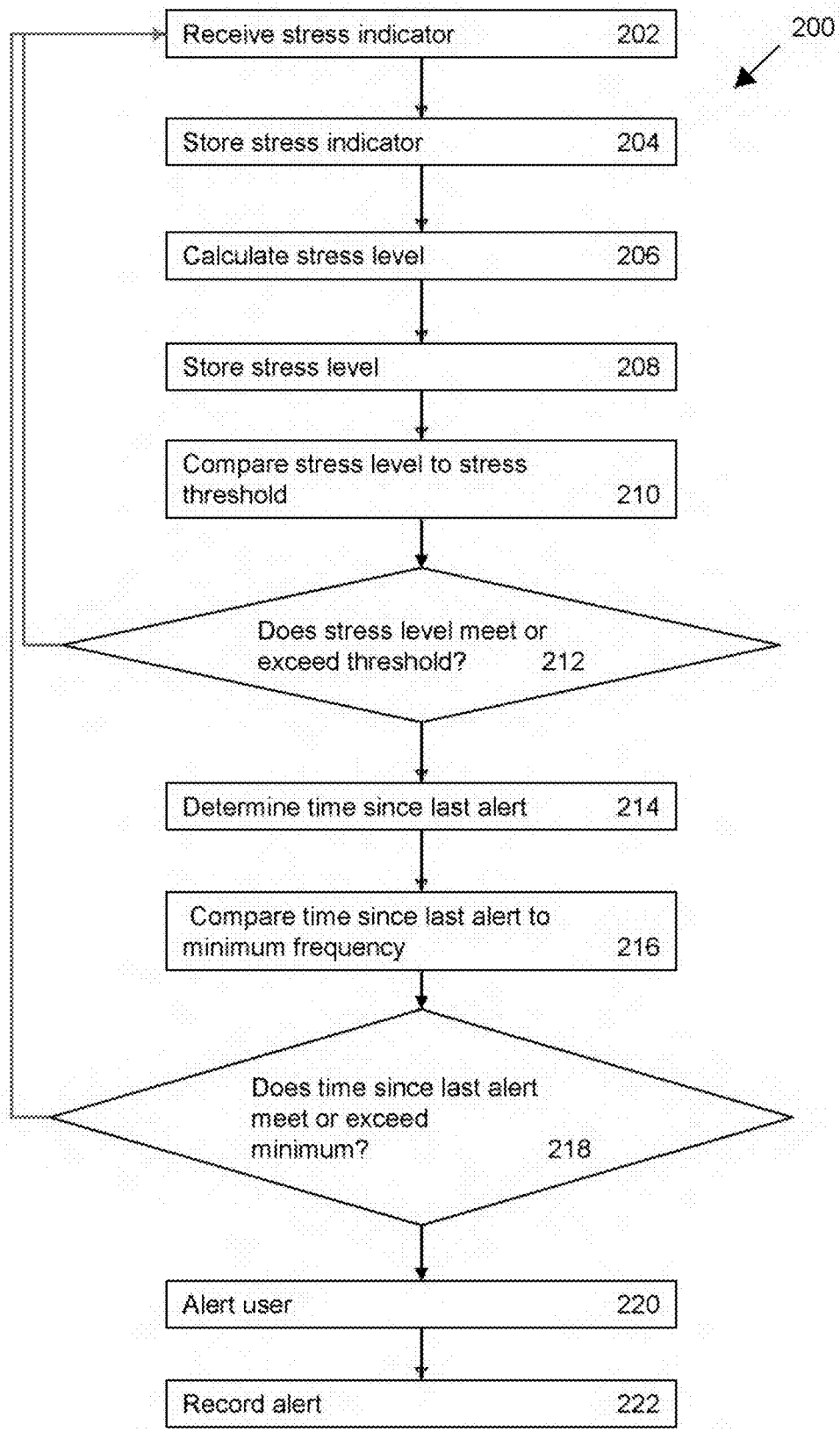
FIG. 3 is a flow diagram of a method of stress detection and intervention of the present disclosure, according to one or more embodiments.

Turning now to FIG. 3, a method 200 of monitoring and interrupting a stress episode is shown, according to one or more embodiments. The method 200 may be performable on, or using, a system of the present disclosure. The method 200 may include the steps of receiving a stress indicator 202; storing the stress indicator 204; calculating a stress level 206; storing the stress level 208; comparing the stress level to a stress threshold 210; determining whether the stress level meets or exceeds the stress threshold 212; determining a time since a last alert 214; comparing the time since the last alert to a minimum frequency 216; determining whether the time since the last alert meets or exceeds the minimum frequency 218; alerting a user 220; and recording the alert 222. In other embodiments, the method 200 may include additional or alternative steps.

Receiving a stress indicator 202 may include receiving a sensor reading from a gyroscope, accelerometer, heart rate monitor, or other user monitoring device. Stress indicators may be received continuously, at intervals, intermittently, or randomly. For example, stress indicators may be received once every second. In some embodiments, stress indicators may be received on demand. For example, a caretaker, family member, medical professional, or another individual may request a stress indicator or may otherwise signal that a stress indicator should be received. In some embodiments, multiple stress indicators may be received simultaneously, substantially simultaneously, or consecutively. As indicated above, stress indicators may be read or sensed by a user device, such as a wearable smartwatch, fitness tracker, heart rate monitor, or other wearable device. Stress indicators may be monitored while a user sleeps in some embodiments, so as to monitor for elevated stress levels during sleep and thus help identify when the user may be experiencing a traumatic nightmare. Stress indicators may be received in any suitable computer readable data format. In some embodiments, one or more stress indicators may be received with multiple data points. For example, a gyroscope stress indicator reading may include values for each of x, y, and z coordinates. Similarly, an accelerometer stress indicator reading may include values for each of x, y, and z coordinates. Received stress indicator(s) may be stored 204 in a database.

From the received stress indicator(s), a stress level may be calculated or otherwise determined 206. In particular, one or more mathematical calculations may be applied to received indicator data to determine a numerical indication of the user's stress level. In some embodiments, the stress level may be calculated based on multiple stress indicators. For example, a numerical stress level for a particular point in time may be calculated based on the user's heart rate, gyroscope, and accelerometer readings for that particular point in time.

In some embodiments, calculating a stress level may include determining a magnitude for one or more stress indicators. That is, where a stress indicator is received as multiple values or coordinates, the coordinates may be combined to determine a magnitude. For example, where a gyroscope stress indicator reading at a particular time (t) includes values for x, y, and z coordinates, the coordinate values may be combined to determine a gyroscope stress indicator magnitude for the particular point in time (t) using the following Equation 1:

$$\text{magnitude}_t = \sqrt{(x_t)^2 + (y_t)^2 + (z_t)^2} \qquad \text{Eq. 1}$$

Where $x_t$, $y_t$, and $z_t$ are coordinate values for a three-axis stress indicator reading at time t. A magnitude for each three-axis gyroscope reading and for each three-axis accelerometer reading may be calculated using the above Equation 1. Other stress indicator readings with multiple-axis datapoints or otherwise having multiple values for a particular time point may be translated into magnitude values using the above equation as well.

Calculating a stress level may additionally include mathematically combining values for one or more stress indicators. That is, for a particular point in time t, sensed or calculated stress indicator values for that particular time may be mathematically combined to determine a value indicative of the user's stress level at the time t. In at least one embodiment, a stress level may be calculated using the following Equation 2:

$$\text{stress level}_t = \frac{\sqrt{W(a_t)^2 + X(b_t)^2 + Y(c_t)^2}}{Z} \qquad \text{Eq. 2}$$

Where $a_t$, $b_t$, and $c_t$ are stress indicator readings for different stress indicators at time t. As a particular example, $a_t$ may be a user's heart rate at time t, $b_t$ may be a gyroscope magnitude as calculated using Equation 1 at time t, and $c_t$ may be an accelerometer magnitude as calculated using Equation 1 at time t. Variables W, X, Y, and Z may be determined based upon a desired result. For example, the variable Z may be selected so that the calculated stress level may fall within a desired range. In particular, it may be desirable to calculate a stress level to fall within a range of 0 to 100. The variable Z may range between 1 and 2 in some embodiments, although other suitable ranges may be used. In at least one embodiment, the variable Z may be, or may be approximately 1.6125. Variables W, X, and Y may be selected to weight the stress indicators as desired. Variables W, X, and Y may all be equal, may all be different, or two of the variables may be equal while the third is different. Variables W, X, and Y may each range between 0 and 1 in some embodiments, although other suitable ranges may be used. In at least one embodiment, variables W and X may be, or may be approximately 0.125, and variable Y may be, or may be approximately, 1. In other embodiments, other suitable equations or mathematical calculations may be used to determine a stress level. In still other embodiments, a user's stress level may be determined using another suitable method. Calculated stress levels may be stored 208 in a database.

In some embodiments, the method may include calculating an average stress level. For example, where stress indicators are sensed every second, and a stress level is calculated every second based on the stress indicators, an average stress level may be calculated for every minute. That is, over a 60-second period, 60 calculated stress levels may be averaged to determine an average stress level for the 60-second period. In other embodiments, an average stress level may be calculated over another suitable time period.

With continued reference to FIG. 3, the method 200 may include comparing the calculated stress level to a stress threshold 210. The stress threshold may be a stored or predetermined value indicating a level at which, or above which, the user may be experiencing a stress episode such as a traumatic nightmare or flashback. In some embodiments, the stress threshold may be a numerical value ranging, for example, between 0 and 100, or another suitable range. In some embodiments, the stress level may be compared to multiple thresholds. For example, a first threshold may signify or indicate a low level of stress, a second threshold may signify or indicate a moderate level of stress, and a third threshold may signify or indicate that the user is likely experiencing a high level of stress. In addition to or alternative to comparing a stress level to a stress level threshold, one or more stress indicators may be compared to a stress indicator threshold. For example, rather than combining accelerometer, gyroscope, and heart rate readings into a single stress level and comparing the stress level to a stress level threshold, individual accelerometer, gyroscope, and heart rate readings may be compared to individual accelerometer, gyroscope, and heart rate thresholds to determine whether a user may be experiencing a stress episode.

In some embodiments, each calculated stress level may be compared to one or more stress thresholds. For example, where a stress level is calculated for each second, the stress level for each second may be compared to one or more thresholds. In other embodiments, the stress level may be averaged over one minute or another suitable time period, and the average stress level may be compared to one or more thresholds.

At step 212, it may be determined whether the stress level for a particular point in time meets or exceeds the stress threshold. If the stress level at a particular point in time does not meet, or does not exceed, the threshold, the method 200 may return to step 202 to continue monitoring stress indicators and comparing stress levels to thresholds to determine whether and when a user's stress level rises to, or above, a stress threshold. If the stress level does meet, or exceed, the threshold, the method 200 may proceed to determine whether an alert should be generated to interrupt the potential stress episode in an attempt to lower the user's stress level.

At step 214, the method 200 may include determining an amount of time since an alert was last initiated or completed. The time since a last alert may be compared to a stored or predetermined minimum frequency 216. The minimum frequency may be a minimum number of seconds, minutes, or hours between consecutive alerts. In this way, it is to be appreciated that while a user is experiencing a stress episode, the user's stress indicators and stress level may be elevated for several consecutive points in time or several consecutive readings. By comparing an amount of time since a last alert to a minimum amount of time between alerts, it may be ensured that the alert is not restarted multiple times within a relatively short period of time. It may be determined whether the amount of time since a last alert (either since the last alert was initiated or since the last alert was completed) meets or exceeds the minimum frequency 218. If the amount of time does not meet or exceed the minimum frequency, the method 200 may return to step 202 to continue monitoring stress indicators and comparing stress levels to thresholds to determine whether and when a user's stress level rises to, or above, a stress threshold. If the amount of time meets or exceeds the minimum frequency, the method 200 may proceed to step 220 to alert the user.

Alerting the user 220 may include initiating one or more alerts or intervention protocols. An alert or intervention protocol may include haptic, audio, and/or visual feedback configured to either wake the user or otherwise draw the user's attention. In some embodiments, alerting the user may include selecting a particular intervention protocol corresponding to a particular alert level or stress level. As described above, for example, different intervention protocols may be defined for low, moderate, and high stress levels, stress thresholds, or alert types. In some embodiments, an intervention protocol may be selected based upon a user's response to previous alerts. For example, where a visual intervention protocol was previously initiated and the user did not respond to the alert, a haptic intervention protocol may be selected for a subsequent alert. In some embodiments, an audio, visual, and/or haptic alert may continue for a predetermined number of seconds or minutes. In other embodiments, the alert may continue until a user interacts with a user device to end the alert or respond to the alert. In other embodiments, the alert may continue until the user's stress indicator(s) indicate a reduction in stress level. The method 200 may additionally include recording an alert event 222 in the database. The time of alert, type of alert, and in some cases duration of alert may be recorded. Moreover, in some embodiments, in addition to or alternative to alerting the user, other users or individuals may be alerted to the possible stress episode. For example, the method may include contacting or notifying a medical professional, caretaker, or family member in response to an indication that the user's stress level has reached or exceeded a stress level threshold.

It is to be appreciated that the steps of the method 200 may be performed in real time or substantially real time. In this way, a user's stress indicator(s) may be monitored in real time, or substantially real time, and the user's stress level may be calculated to determine when the user may be experiencing, or may be about to experience, a stress episode. Based on the stress indicators and/or stress level, an intervention protocol may be initiated to wake the user or to otherwise draw the user's attention in an effort to reduce the user's stress. Where the user is sleeping and experiencing a traumatic nightmare during sleep, an alert may be initiated to wake the user, draw the user out of a REM sleep cycle, or to otherwise disrupt or interrupt the traumatic nightmare. The method 200 may thus help to stop, cut short, or preempt traumatic nightmares, flashbacks, anxiety attacks, and/or other stress episodes.

One skilled in the art will recognize that there are a variety of ways a system of the present disclosure could determine whether to intervene with what may be a stress episode. For example, one could use a machine learning algorithm trained on sensor values and hand-tagged nightmares (or other stress episodes) to learn when it is appropriate to intervene. Such machine learning may be used instead of, or in addition to, a stress level threshold. Moreover, a stress threshold may be computed or determined using alternative methods. A stress threshold may be based on one or more of any number of past samples, sensor values, stress values, etc. The minimum and maximum number of samples used to compute it could vary. The method used to select the stress threshold (e.g. a percentile) could also vary.

One skilled in the art will also recognize that a method of the present disclosure may include monitoring stress indicators and/or stress levels without intervention. This may be useful in a variety of settings where one is trying different approaches, such as a drug trial, to address traumatic nightmares (or other stress episodes) and using an embodiment of the present disclosure to see what impact or effectiveness those approaches are having on the individual.

FIGS. 7-21 illustrate some embodiments of methods or processes that may be performed by, or using, a system of the present disclosure for monitoring a user's stress level and interfering with a stress episode. In particular, FIGS. 7-21 demonstrate a user's interaction with systems and methods of the present disclosure, according to some embodiments.

Figure 7:
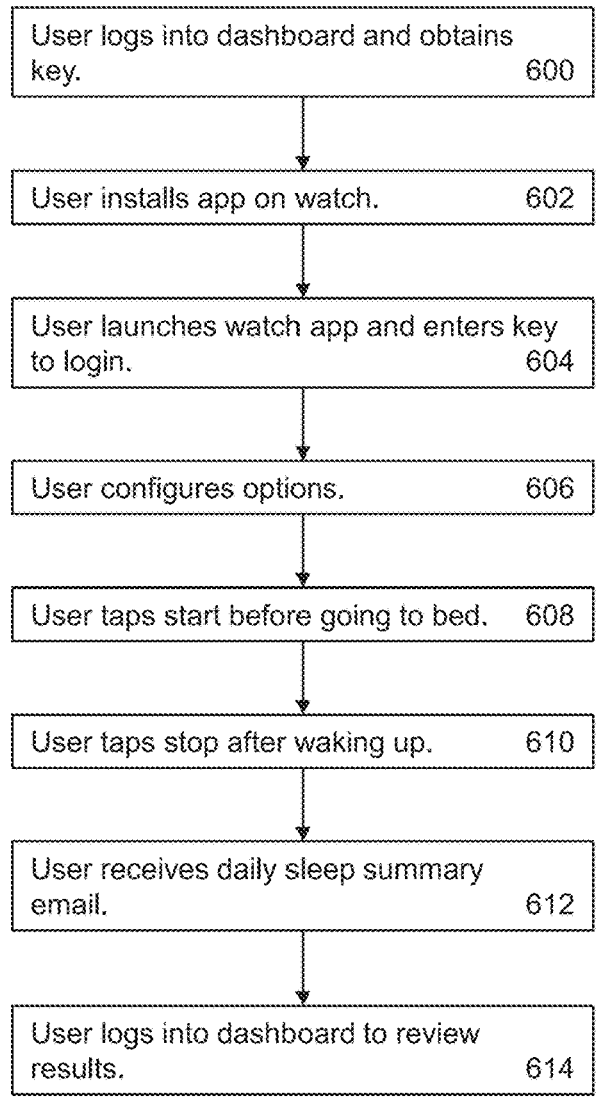
FIG. 7 is a flow diagram of a method of using a system of the present disclosure for stress monitoring, according to one or more embodiments.

FIG. 7 illustrates a flow diagram of a user interaction with a system of the present disclosure for sleep monitoring. At step 600, a user may log into the dashboard page 300 via a smartphone, desktop or laptop computer, or other user device, and may receive a login key. At step 602, the user may install a software application on the user's smartwatch or other wearable user device. At step 604, the user may launch the software application on the user's smartwatch and may enter the previously received login key. At step 606, the user may configure options via the software application. Configurable options may include stress thresholds, type of monitoring to be performed, frequency of monitoring, alert levels, intervention protocols, and other configurations. To initiate stress indicator monitoring, the user may tap a "start" button or otherwise initiate monitoring via the software application before going to bed at step 608. At step 610, the user may tap a "stop" button or may otherwise end monitoring via the software application after waking up. At step 612, the user may receive a daily, or other suitable time interval, sleep summary via an email, text message, push notification, popup message, or other suitable communication. At step 614, the user may log into the dashboard page 300 to review data, such as stress indicator received by the system while the user was sleeping, stress level data computed by the system while the user was sleeping, and alert data relating to intervention protocols that may have been initiated while the user was sleeping.

Figure 8:
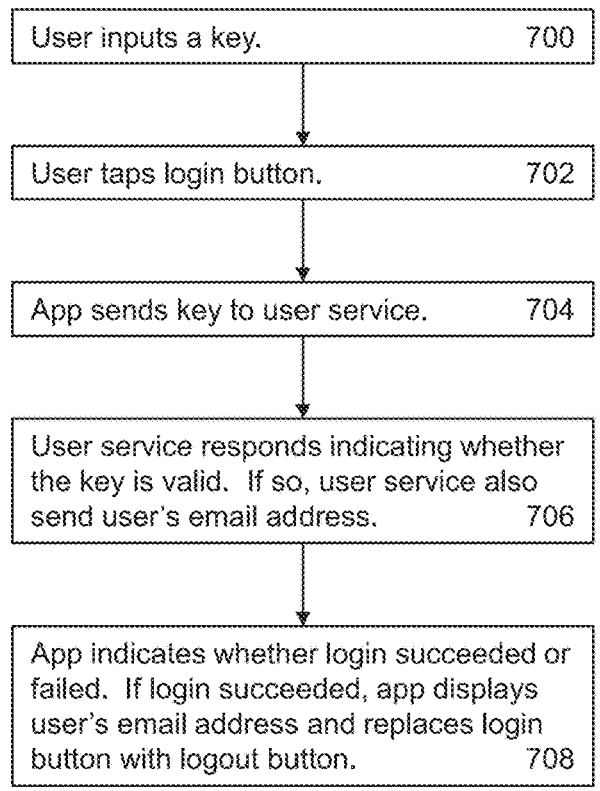
FIG. 8 is a flow diagram of a login method of the present disclosure, according to one or more embodiments.

FIG. 8 is a flowchart for securely logging into the software application in an embodiment of the present disclosure. The software application may be an app provided on a user device, such as a smartphone, smart watch, fitness tracker, or other user device. At step 700, the user may input a key via the software application. The key may be a code or other device received via another user interface and/or another user device. For example, as indicated above with respect to FIG. 7, the user may request a key via a dashboard page on a computing device. At step 702, the user may tap a login button on the software application. At step 704, the app may send the key to the user service 412. At step 706, the user service 412 may respond indicating whether the key is valid. If so, the user service 412 may also send the user's email address or another identifier. At step 708, the software application may indicate whether the login succeeded or failed. If login succeeded, the application may display the user's email address and replace the login button with a logout button on the user device. It is to be appreciated that secure login or user authentication may be performed using different security mechanisms or protocols. For example, the user might provide a username/password, key, code, fingerprint, voiceprint, facial image, etc. The user may supply this information via a touchscreen, keypad, microphone, camera, etc.

Figure 9:
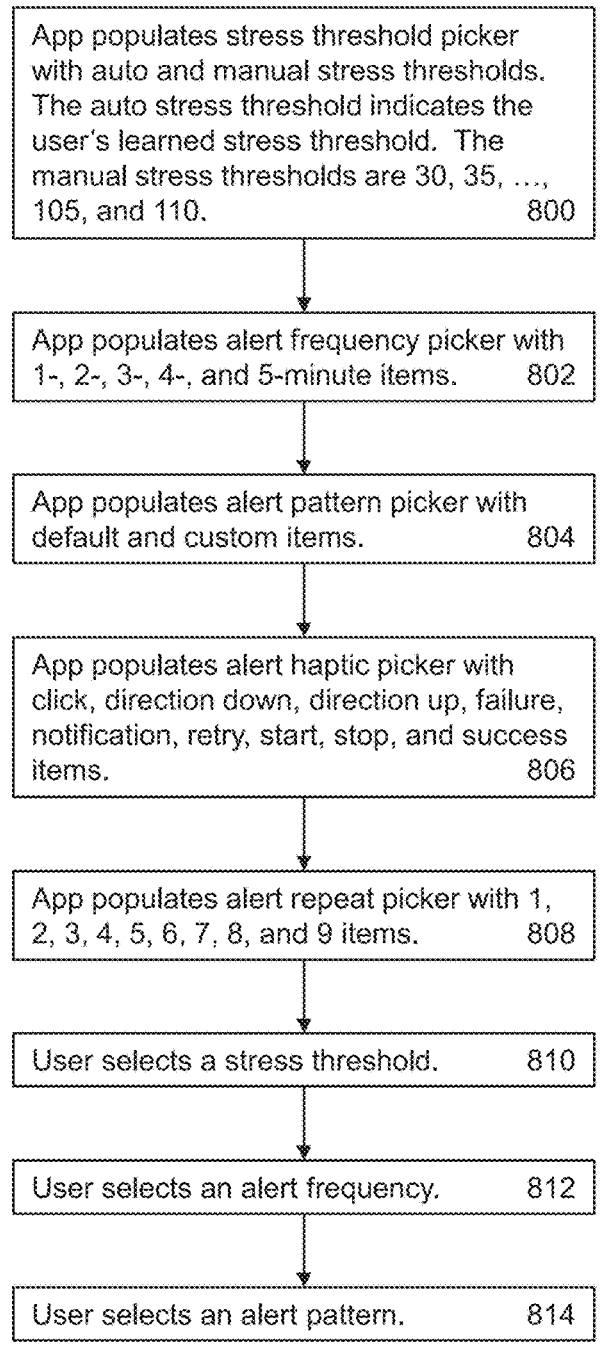
FIG. 9 is a flow diagram of a method of configuring user settings of the present disclosure, according to one or more embodiments.

FIG. 9 is a flowchart for configuring user settings, according to one or more embodiments. At step 800, the software application, which may be an app on a user device such as a smart watch or other wearable or personal device, may populate a stress threshold picker with options for automatically selected and/or manually selected stress thresholds. For the automatically selected stress threshold, the app may indicate the user's learned stress threshold based on historical stress indicator data. The user may choose to use the learned stress threshold. For the manually selected stress threshold, the app may present the user with an option to set or designate one or more stress thresholds. In some embodiments, one or more stress thresholds may default to a present value (which may or may not be the learned stress threshold). At step 802, the app may populate an alert frequency picker, where the user may choose from an alert frequency of 1, 2, 3, 4, or 5 minutes, or another suitable frequency, between alerts. The selected alert frequency may be a minimum time between intervention protocols. At step 804, the app may populate an alert pattern picker with default and/or custom items. The app may have default intervention patterns or protocols. An alert pattern or protocol may relate to a haptic, audio, and/or visual alert protocol configured to wake a user or otherwise to draw a user's attention. At step 806, the app may populate an intervention protocol picker. For example, where an intervention protocol may include haptic feedback, the app may populate an alert haptic picker with click, direction down, direction up, failure, notification, retry, start, stop, and success items. The app may use predefined haptics like these or allow the user to generate custom haptics for intervention. At step 808, the app may populate an alert repeat picker with, for example, 1, 2, 3, 4, 5, 6, 7, 8, and 9 items. The app may repeat the selected alert haptic or other intervention protocol this number of times when intervening. At step 810, a user may select a stress threshold using the stress threshold picker. At step 812, the user may select an alert frequency using the alert frequency picker. At step 814, the user may select an alert pattern using the alert pattern picker. One skilled in the art will recognize that the app could present different stress thresholds, alert frequencies, and alert repeat pickers than those listed above. Also, the interface could provide a variety of methods for customizing alerts such as configuring the duration and intensity of vibration patterns and gaps between them.

Figure 10:
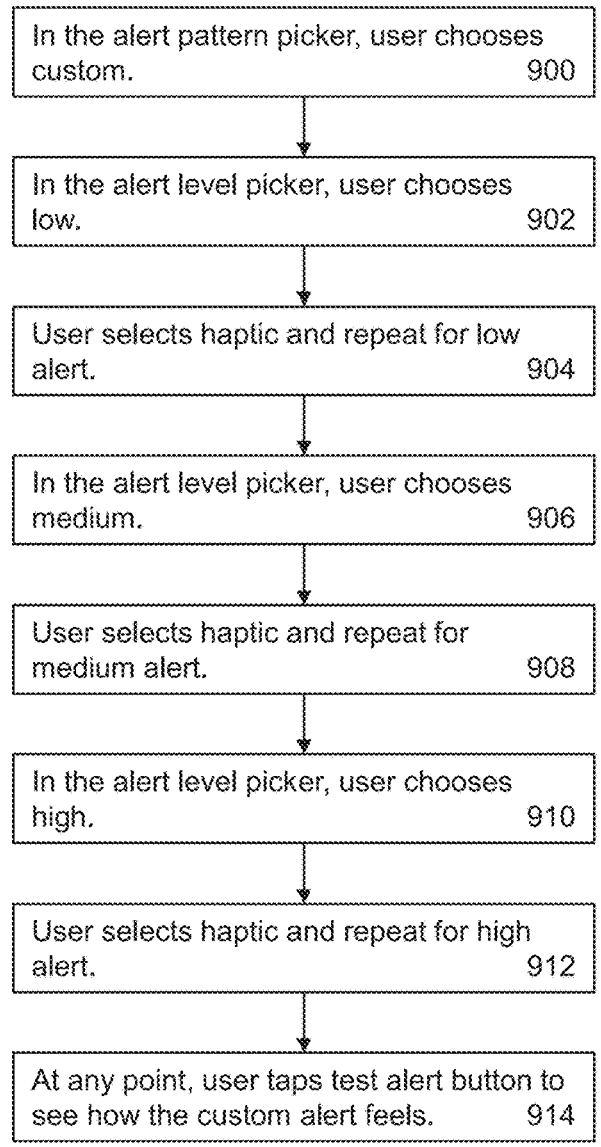
FIG. 10 is a flow diagram of a method of customizing user alerts of the present disclosure, according to one or more embodiments.

FIG. 10 is a flowchart for customizing the app's alerts in an embodiment of the present disclosure. At step 900, in an alert pattern picker, the user may choose to set a custom alert. Additionally or alternatively, the user may have an option to select default or preset alert patterns or protocols. At step 902, in an alert level picker, the user may choose "low" to set an alert pattern or protocol for a low alert level. At step 904, the user may choose one or more haptic, audio, and/or visual alerts. For example, the user may select a type or intensity of vibration, may select an audio sound and volume, and/or may select a light or screen to display. The user may also select a repetition count for the low alert level—that is, the number of times the low alert may repeat when the low alert protocol is initiated. At step 906, in an alert level picker, the user may choose "medium" to set an alert pattern or protocol for a medium alert level. At step 908, the user may choose one or more haptic, audio, and/or visual alerts, and may select a repetition count for medium alert level. At step 910, in an alert level picker, the user may choose "high" to set an alert pattern or protocol for a high alert level. At step 912, the user may choose one or more haptic, audio, and/or visual alerts, and repetition count for high alert level. At step 914, at any point while configuring custom alerts, a user may tap a test alert button to try out the custom alert. While described with three levels, it is to be appreciated that more or fewer alert levels may be used in other embodiments.

Figure 11:
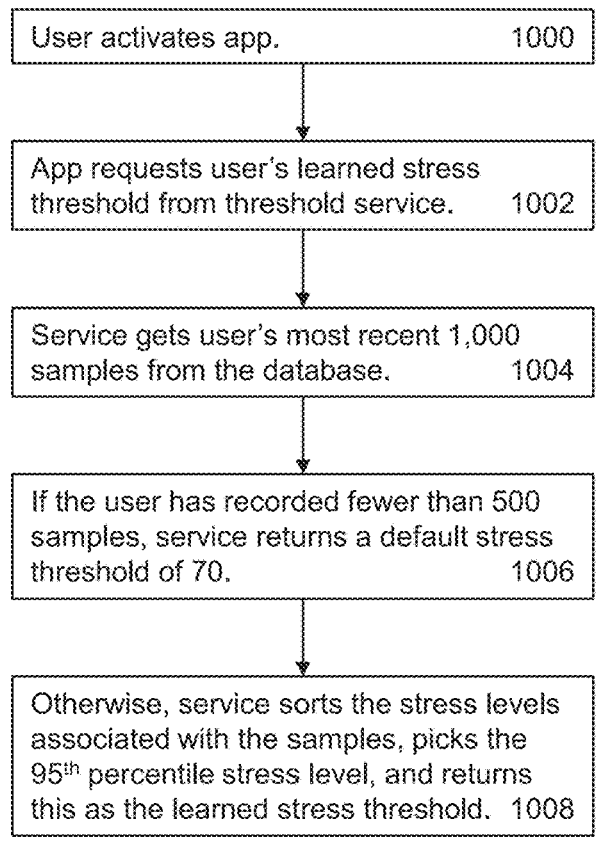
FIG. 11 is a flow diagram of a method of customizing a stress threshold of the present disclosure, according to one or more embodiments.

FIG. 11 is a flowchart for customizing a learned stress threshold in an embodiment of the present disclosure. At step 1000, the user may activate the software application on the user's user device, computing device, wearable device, or other user device. At step 1002, the application may request the user's learned stress threshold from threshold service 410. At step 1004, the threshold service 410 may retrieve the user's most recent 1,000, or another suitable number of, calculated stress levels from the database 110. At step 1006, if the user has recorded fewer than 500 samples (or sensed data points), or fewer than another suitable number of samples, the threshold service 410 may return a default stress threshold. In some embodiments, the stress threshold may be or include a numerical value ranging between 0 and 100 or another suitable range. In such embodiments, the default stress threshold may have a numerical value ranging, for example, between 40 and 100, or between 50 and 90, or between 60 and 80. In some embodiments, the default stress threshold may be 70 or approximately 70. At step 1008, if the user has recorded at least 500 samples, or another suitable minimum number of samples, the threshold service 410 may sort the stress levels associated with the samples, pick the 95th, or other suitable, percentile stress level, and return this as the user's learned stress threshold value.

Figure 12:
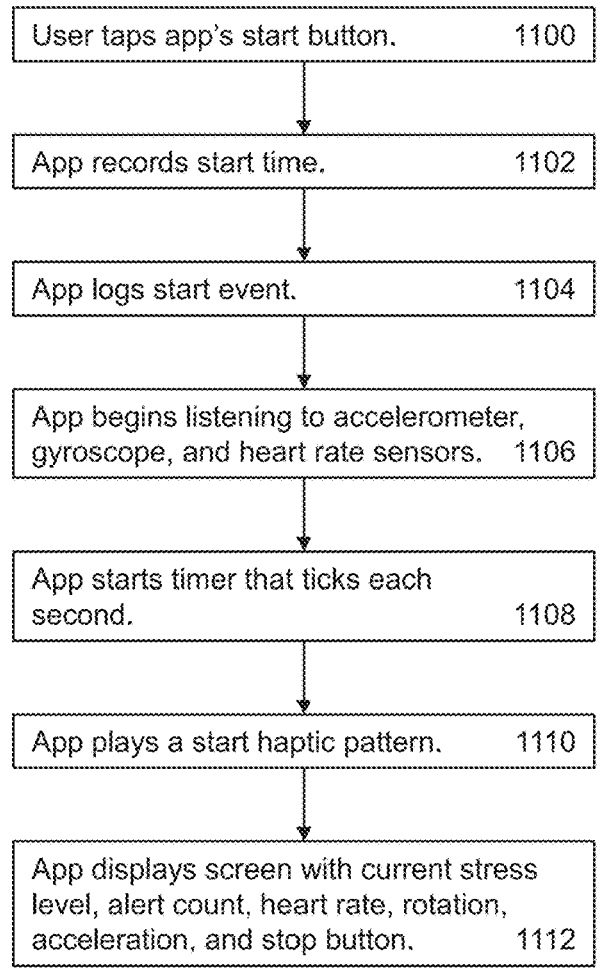
FIG. 12 is a flow diagram of a method of initiating a stress monitoring session of the present disclosure, according to one or more embodiments.

FIG. 12 is a flowchart for initiating stress level monitoring using a software application of the present disclosure. At step 1100, the user may tap a start button to begin a monitoring process. At step 1102, a start time of when monitoring was initiated may be recorded. At step 1104, the event service 400 may be used to log the start event. Once monitoring begins, sensors, such as a gyroscope, accelerometer, heart rate monitor, and/or other sensors associated with a user device, which may be a wearable device, may sense one or more stress indicators 1106 and may send sensed data to the database. As indicated above, during monitoring, data for each stress indicator may be sensed intermittently, at intervals, randomly, continuously, or on demand. In at least one embodiment, each sensor may collect stress indicator data once per second. At step 1108, a timer may be started for timing sensor readings. At step 1110, a haptic pattern may be initiated as, or as part of, an intervention protocol upon an indication that the user may be experiencing a stress episode. At step 1112, during monitoring operations, the user's current or most recent stress level and/or sensed stress indicator values may be displayed via a user interface on a user device, which may be a wearable device. Additionally, a "stop" button may be displayed such that the user may end monitoring when desired.

It is to be appreciated that, in some embodiments, monitoring could be initiated and ended automatically and without the use of "start" and "stop" buttons. For example, the software application may initiate monitoring stress indicators when the user removes the user device from a charger, and may stop monitoring when the user replaces it on the charger. Alternatively, the application may detect when the user is resting (e.g. based on accelerometer readings) and may initiate and stop monitoring appropriately based on such indication.

Figure 13:
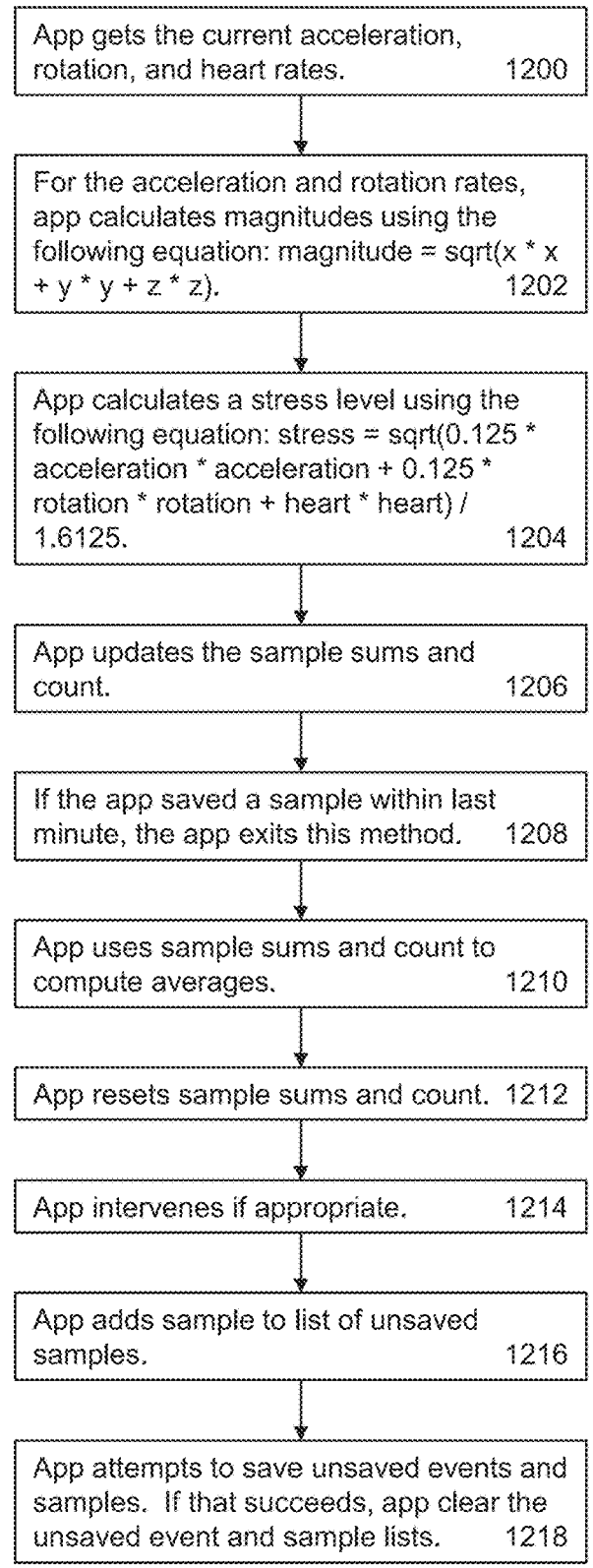
FIG. 13 is a flow diagram of method of stress monitoring of the present disclosure, according to one or more embodiments.

FIG. 13 is a flowchart for a monitoring process performed using a software application of the present disclosure. At step 1200, the app may receive one or more stress indicator values from one or more sensors, such as from an accelerometer, gyroscope, and/or heart rate monitor. At step 1202, a magnitude may be calculated for stress indicators received as coordinate values. For example, where acceleration and rotation are received as x, y, and z coordinate values for a particular point in time, the coordinate values may be used to calculate corresponding acceleration and rotation magnitudes for the point in time using, for example, Equation 1, as discussed above. At step 1204, a stress level may be calculated for the particular time using the received stress indicators and Equation 2, or another suitable mathematical calculation or transformation.

As indicated above, in some embodiments, an average stress level and/or average stress indicator(s) may be calculated over a time interval. A running sample sum totaling sample data received for the user's stress level and/or stress indicators may be maintained for the time interval. A running sample count may total a number of samples included in the current sample sum. With continued reference to FIG. 13, at step 1206, upon receiving and logging sample data for a point in time, the software application may update a sample sum (i.e., a running total for stress level and/or each stress indicator) and a sample count (i.e., number of samples). In one embodiment, an average stress level over one minute (60 seconds) may be calculated using stress indicator data collected during that time period. Where samples are collected each second, 60 samples may be averaged together to determine an average stress level over one minute. As an example, at step 1208, if the app saved a sample within the last minute, the app may exit this method. Otherwise, at step 1210, a stored sample sum (60 samples) and a sample count (sum of all 60 stress levels for the 60 second period) may be used to compute an average stress level over the 60-second period. At step 1212, the app may reset the sample sums and count for the next minute. At step 1214, the app may intervene if appropriate. At step 1216, the app may add the sample to a list of unsaved samples. At step 1218, the app may attempt to save unsaved events and samples. If that succeeds, the app may clear the unsaved event and sample lists. It is to be appreciated that in other embodiments, an average stress level may be calculated over a different time interval. Moreover, in some embodiments, an average stress indicator for one or more stress indicators (e.g. rotation, acceleration, heart rate, or others) may be calculated over a suitable time interval in addition or alternative to an average stress level.

Figure 14:
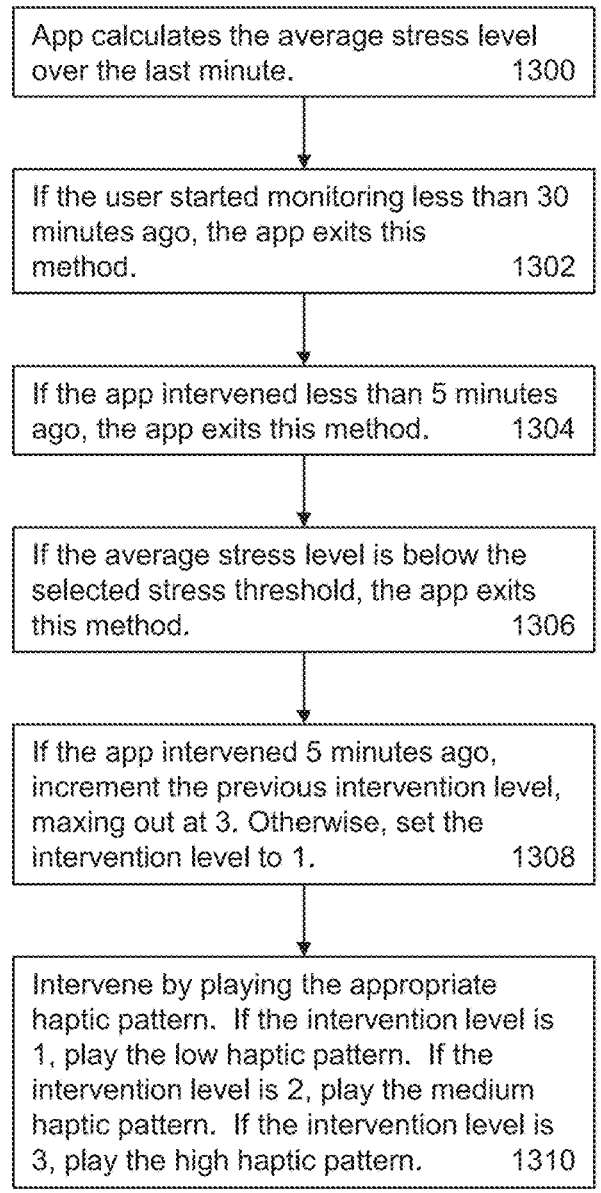
FIG. 14 is a flow diagram of method of determining whether to execute an intervention protocol of the present disclosure, according to one or more embodiments.

FIG. 14 is a flowchart for a system of the present disclosure determining whether to execute an intervention protocol. At step 1300, an average stress level over the past 60 seconds, or other suitable or desirable time interval, may be calculated. That is, as stress indicators are sensed every second, for example, a stress level may be calculated for each second in time. The 60 calculated stress levels over a minute may then be averaged to determine an average stress level each minute during monitoring. At step 1302, if monitoring has been initiated relatively recently, it may be determined that an intervention protocol should not be initiated. For example, if monitoring was initiated less than 30 minutes ago, or other suitable or desirable time interval, the computing device may exit this method. At step 1304, if an intervention protocol was initiated or completed relatively recently, it may be determined that an intervention protocol should not be initiated. For example, if an intervention protocol was initiated less than 5 minutes ago, or other suitable or desirable time interval, the computing device may exit this method. At step 1306, the calculated average stress level may be compared to a stress threshold to determine whether intervention is appropriate. For example, if the average stress level over the last minute, or other suitable or desirable time interval, is below the selected stress threshold, the computing device may exit this method. At step 1308, an alert level may be selected. For example, if an intervention protocol was initiated or completed 5-10 minutes ago, or other suitable or desirable time interval, in incrementally higher alert level may be chosen over the previous alert level. Otherwise, a default low alert level may be selected. In some embodiments, as discussed above, an alert level may be selected based upon a stress level or based upon how high the stress level is above one or more thresholds. At step 1310, an intervention protocol may be initiated to alert the user.

One skilled in the art will recognize that one could use durations different from those listed above. For example, one might wait 15 minutes or 1 hour before first intervening. Also, one might intervene every 1 minute or every 10 minutes if stress levels remain high. Moreover, in some embodiments, intervention protocols may be randomized to prevent a patient from becoming accustomed to a given intervention pattern.

Figure 15:
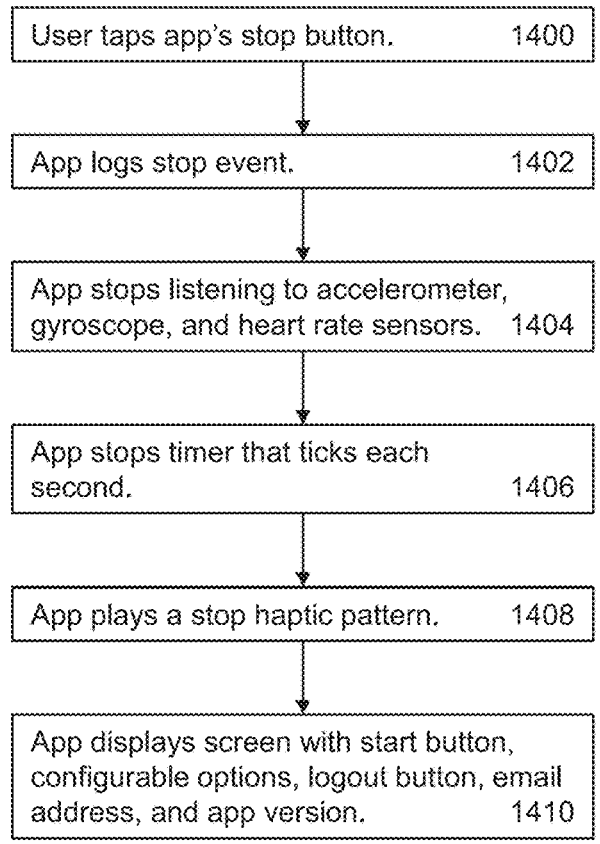
FIG. 15 is a flow diagram of a method of ending a stress monitoring session of the present disclosure, according to one or more embodiments.

FIG. 15 is a flowchart to end a monitoring process, according to some embodiments. At step 1400, a user may tap the app's "stop" button or may otherwise signal through a user interface that monitoring should cease. At step 1402, the app may use the event service 400 to log the stop event. At step 1404, the app may stop listening to the accelerometer, gyroscope, heart rate monitor, and/or other sensors. At step 1406, the app may stop the timer that ticks each second. At step 1408, the app may play a stop haptic pattern. At step 1410, the app may display a screen with one or more of a "start" button, configurable options, logout button, email address, and app version.

Figure 16:
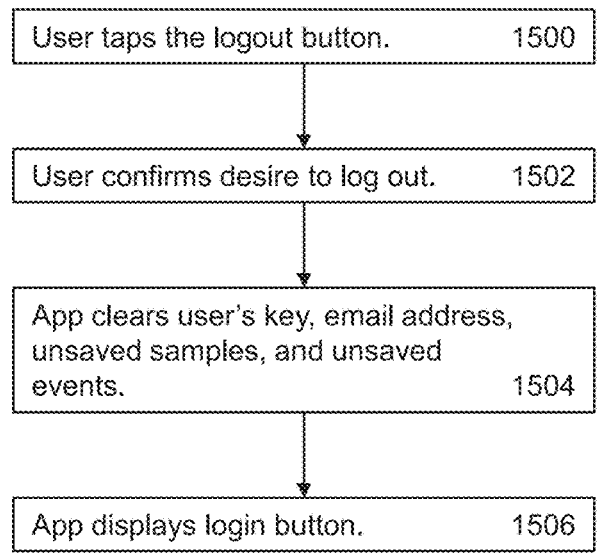
FIG. 16 is a flow diagram of a logout method of the present disclosure, according to one or more embodiments.

FIG. 16 is a flowchart for logging out of a software application of the present disclosure, such as an app on a smartwatch, smartphone, or other user device. At step 1500, a user may tap a logout button. At step 1502, the user may confirm his or her desire to log out. At step 1504, the app may clear the user's key, email address, unsaved samples, and unsaved events. At step 1506, the app may display a login button.

Figure 17:
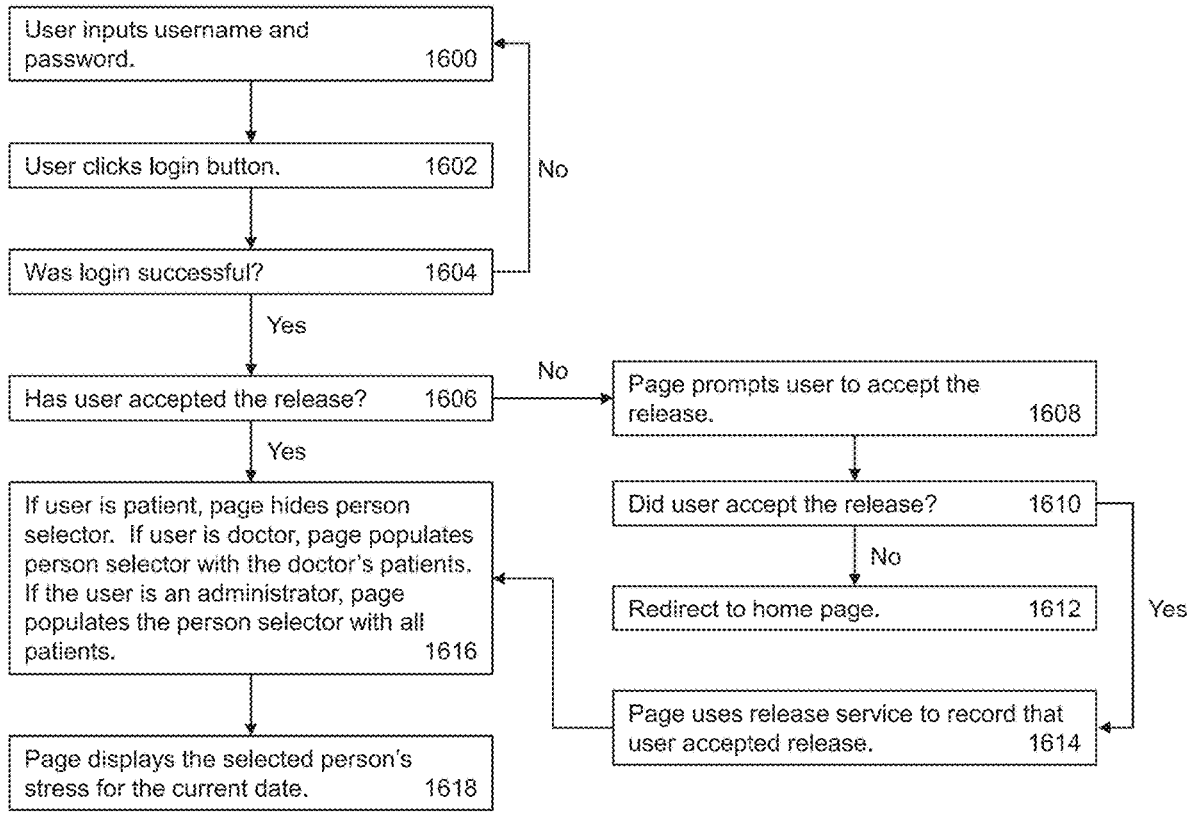
FIG. 17 is a flow diagram for a method of logging into a dashboard page of the present disclosure, according to one or more embodiments.

FIG. 17 is a flowchart for logging into the dashboard page 300 of a user interface in an embodiment of the present disclosure. The dashboard page 300 may be accessible via a user device, such as a wearable device, personal device, computing device, or other user device, or a device connected via network 106 with the system, including for example, server 108. At step 1600, the user may input a username and password. At step 1602, the user may click a login button. At step 1604, the page may use the user service 412 to determine whether the login was successful. If login failed, the page may return to step 1600. If login succeeded, the page may proceed to step 1606. At step 1606, the page may use the release service 404 to determine whether user has accepted release. If the user has accepted the release, the page may proceed to step 1616. Otherwise, the page may proceed to step 1608. At step 1608, the page may prompt user to accept the release. At step 1610, the page may determine whether the user accepted the release. If the user accepted the release, the page may proceed to step 1614. Otherwise, the page may proceed to step 1612. At step 1612, since the user rejected the release, the app may redirect the user to the home page. At step 1614, since the user accepted the release, the app may use the release service 404 to record the release acceptance date. At step 1616, the page may update the person selector as appropriate. If the user is a patient, the page may hide the person selector. If user is a doctor, the page may populate the person selector with the doctor's patients. If the user is an administrator, the page may populate the person selector with all patients. At step 1618, the page may use the sample service 406 to obtain and display the selected person's stress levels for the current date, or other suitable time period.

Figure 18:
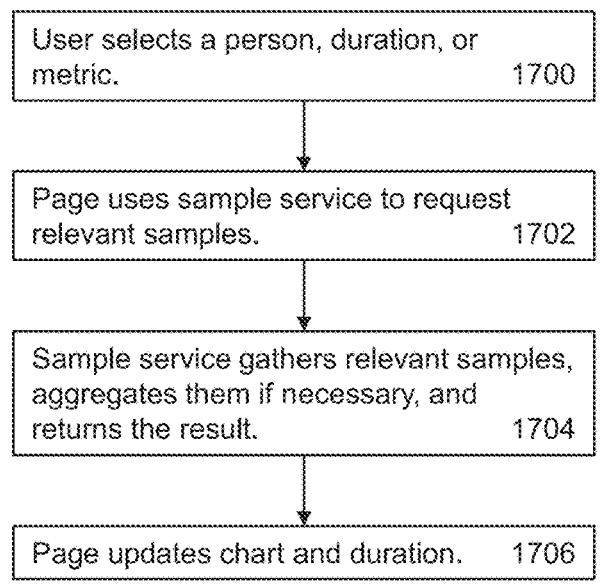
FIG. 18 is a flow diagram for a method of updating a dashboard page of the present disclosure, according to one or more embodiments.

FIG. 18 is a flowchart for updating the dashboard page 300 of a user interface in an embodiment of the present disclosure. At step 1700, a user may select a person, duration, or metric. At step 1702, the page may use the sample service 406 to request relevant samples. At step 1704, the sample service 406 may gather relevant samples, aggregate them if necessary, and return the result. For accelerometer, gyroscope, heart rate, and stress levels, the sample service 406 may aggregate values by calculating the average sensor value during a 24-hour period, or other suitable time period. For intervention levels, the sample service 406 may aggregate values by counting the number of interventions during, for example, a 24-hour period. At step 1706, the page may update the chart to show the values returned by the sample service 406. The page may also update the displayed chart duration.

One skilled in the art will recognize that there are many ways to present sensor, stress, and intervention data to users. One could support different time scales, zooming in on data, exporting data for analysis in other programs, etc.

Figure 19:
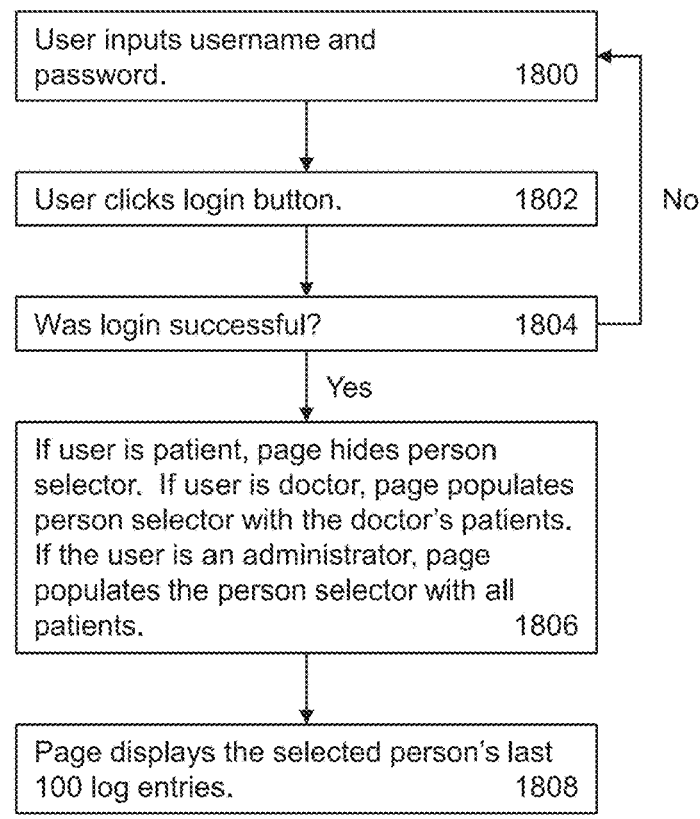
FIG. 19 is a flow diagram for a method of logging into a log page of the present disclosure, according to one or more embodiments.

FIG. 19 is a flowchart for logging into the log page 302 of a user interface in an embodiment of the present disclosure. The log page 302 may be accessible via a user device, such as a wearable device, personal device, computing device, or other user device, or a device connected via network 106 with the system, including for example, server 108. At step 1800, the user may input a username and password. At step 1802, the user may click a login button. At step 1804, the page may use the user service 412 to determine whether the login was successful. If login failed, the page may return to step 1800. If login succeeded, the page may proceed to step 1806. At step 1806, the page may update the person selector as appropriate. If the user is a patient, the page may hide the person selector. If user is a doctor, the page may populate the person selector with the doctor's patients. If the user is an administrator, the page may populate the person selector with all patients. At step 1808, the page may use the event service 400 to obtain and display the selected person's last 100, or other suitable number, log entries.

Figure 20:
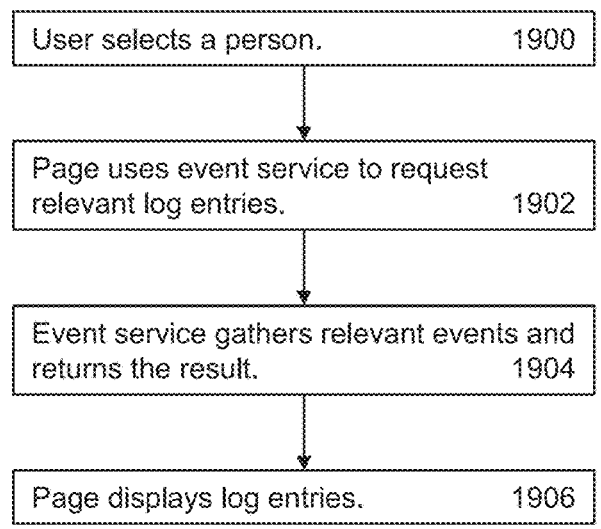
FIG. 20 is a flow diagram for a method of updating a log page of the present disclosure, according to one or more embodiments.

FIG. 20 is a flowchart for updating the log page 302 of a user interface in an embodiment of the present disclosure. At step 1900, a user may select a person. At step 1902, the page may use the event service 400 to request relevant log entries or events. At step 1904, the event service 400 may gather relevant log entries or events and send the result. At step 1906, the page may display the returned log entries or events.

Figure 21:
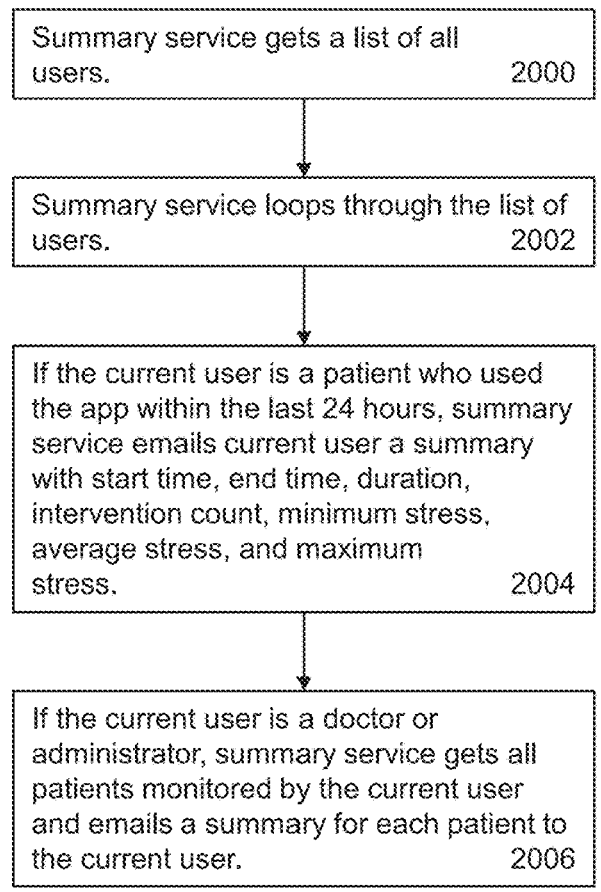
FIG. 21 is a flow diagram for a method of sending a data summary of the present disclosure, according to one or more embodiments.

FIG. 21 is a flowchart for sending a daily, or other suitable or desirable time interval, summary email or other suitable communication in an embodiment of the present disclosure. At step 2000, the summary service 408 may get a list of all users. At step 2002, the service may begin looping through the user list. At step 2004, if the current user is a patient who used the app within the last 24 hours, the service may, for example, email the current user a summary over this period including one or more of a start time, end time, duration, intervention count, minimum stress, average stress, and maximum stress. At step 2006, if the current user is a doctor or administrator, the service may get all patients monitored by the current user and, for example, email the current user a summary for each of these patients.

One skilled in the art will recognize that there are several ways one might deliver summary data to patients, doctors, and administrators. Instead of sending an email, the app could send a notification that would appear on the user's mobile device. Also, the summary could include many other types of information such as, but not limited to, the effectiveness of different intervention patterns for different users As indicated above, a system of the present disclosure may provide a user interface via a software application. A user interface of the present disclosure may be accessible via a wearable device, user device, computing device, and/or other device. While the user interface may be accessible via a software application in some embodiments, in other embodiments a user interface of the present disclosure may be or include a web-based interface accessible using an Internet browser, for example. In some embodiments, a user may have different interfaces on different devices. Each interface may provide different screens and pages and/or different functionality. FIGS. 22-26 show one embodiment of a user interface that may be accessible via a smartwatch or other wearable device, for example.

Figure 22:
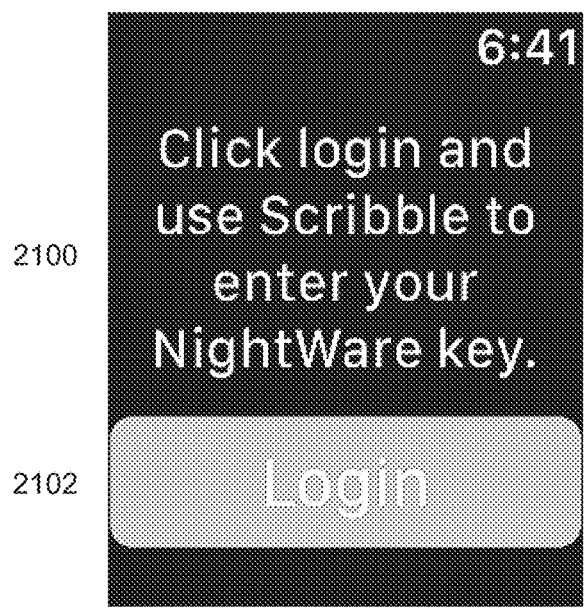
FIG. 22 is a screenshot of a login page of a user interface for a wearable device of the present disclosure, according to one or more embodiments.

FIG. 22 is an example login interface in an embodiment of the present disclosure. The interface may include one or more of instructions 2100 and a login button 2102. A user may use this interface to, for example, initiate logging into a software application on the wearable device.

Figure 23:
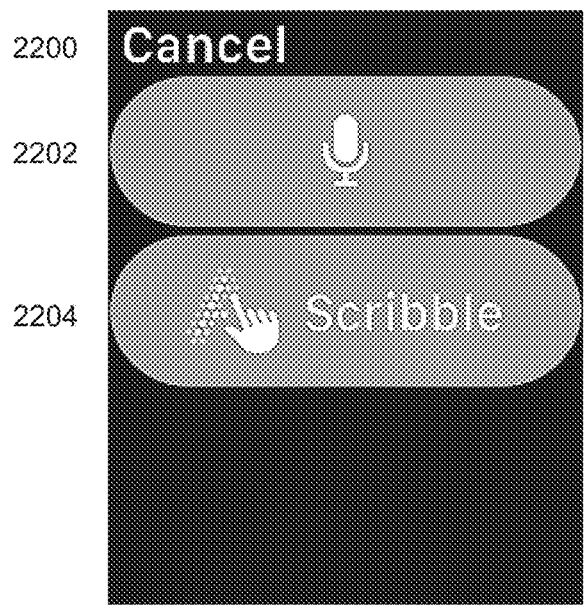
FIG. 23 is a screenshot of a user input page of a user interface for a wearable device of the present disclosure, according to one or more embodiments.

FIG. 23 is an example input interface in an embodiment of the present disclosure, which may allow a user to input an access key, for example. The interface may include one or more of a cancel button 2200, a voice input button 2202, and a text input button 2204. A user may use this interface to, for example, select an input method when logging into the software application.

Figure 24:
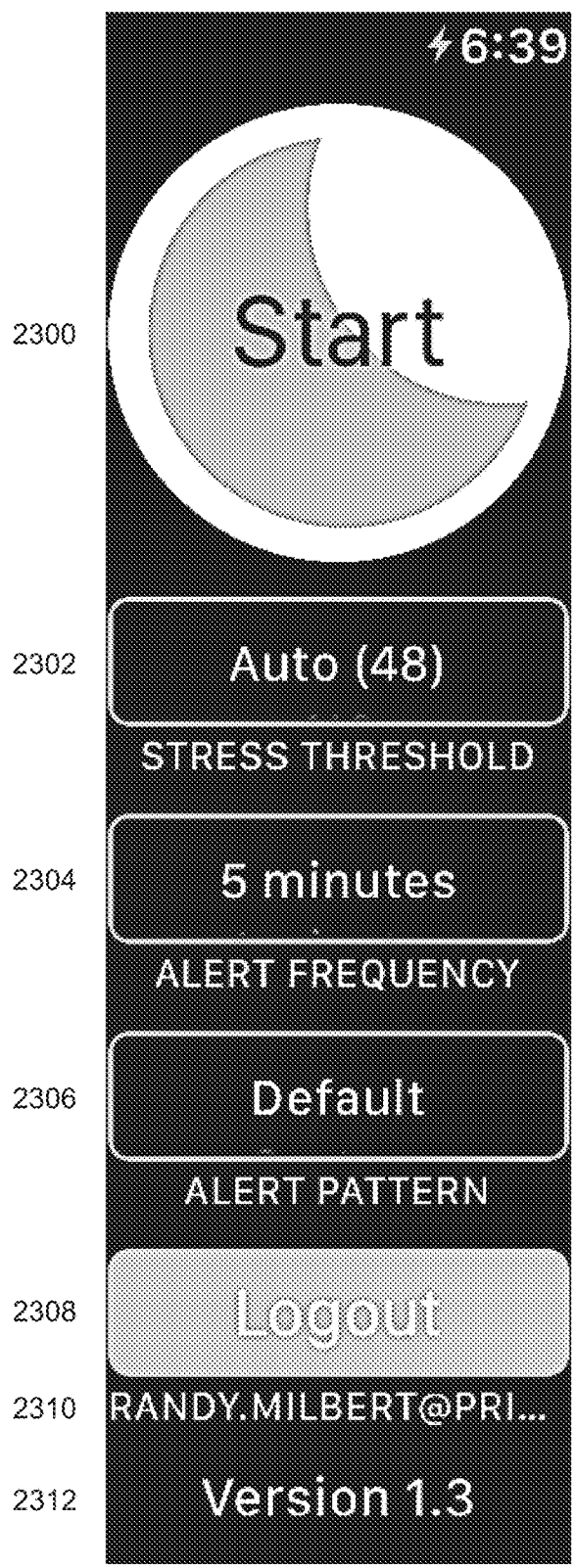
FIG. 24 is a screenshot of a home page of a user interface for a wearable device of the present disclosure, according to one or more embodiments.

FIG. 24 is an example home interface in an embodiment of the present disclosure. The interface may include one or more of a start button 2300, a stress threshold picker 2302, an alert frequency picker 2304, an alert pattern picker 2306, a logout button 2308, a user e-mail address 2310, and a version indication 2312. A user may use this interface to, for example, start monitoring, configure settings of the software application, or logout, as described above.

Figure 25:
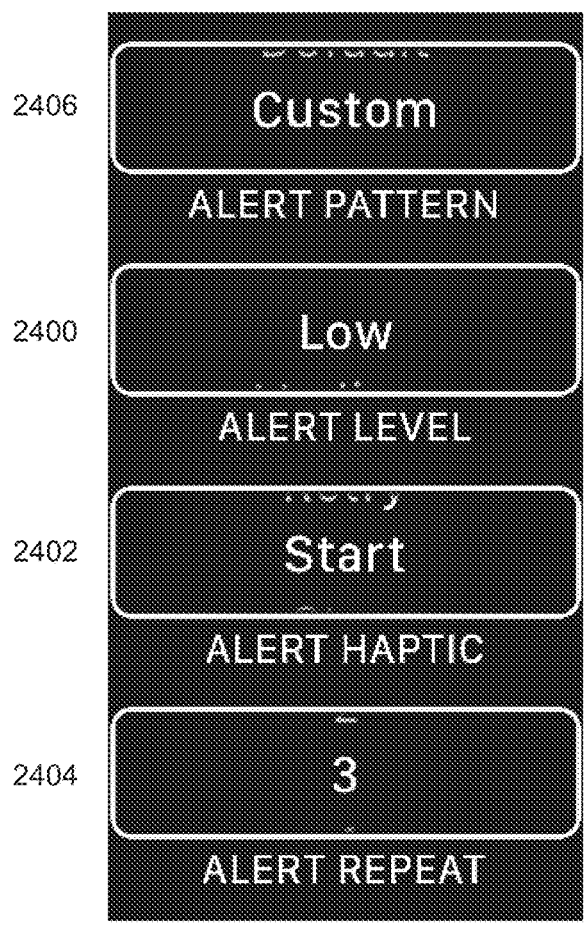
FIG. 25 is a screenshot of a custom alert page of a user interface for a wearable device of the present disclosure, according to one or more embodiments.

FIG. 25 is an example interface for customizing alerts in an embodiment of the present disclosure. In particular, where a user selects the alert pattern picker 2306 from the home screen of FIG. 24, the user may be presented with the customizing screen of FIG. 25. An alert pattern picker 2406 may allow the user to select custom or default. When a user selects custom, the interface may display one or more of an alert level picker 2400, an alert haptic picker 2402, and an alert repeat picker 2404. A user may use this interface to, for example, configure custom low, medium, and high interventions for execution on the wearable device, as described above.

Figure 26:
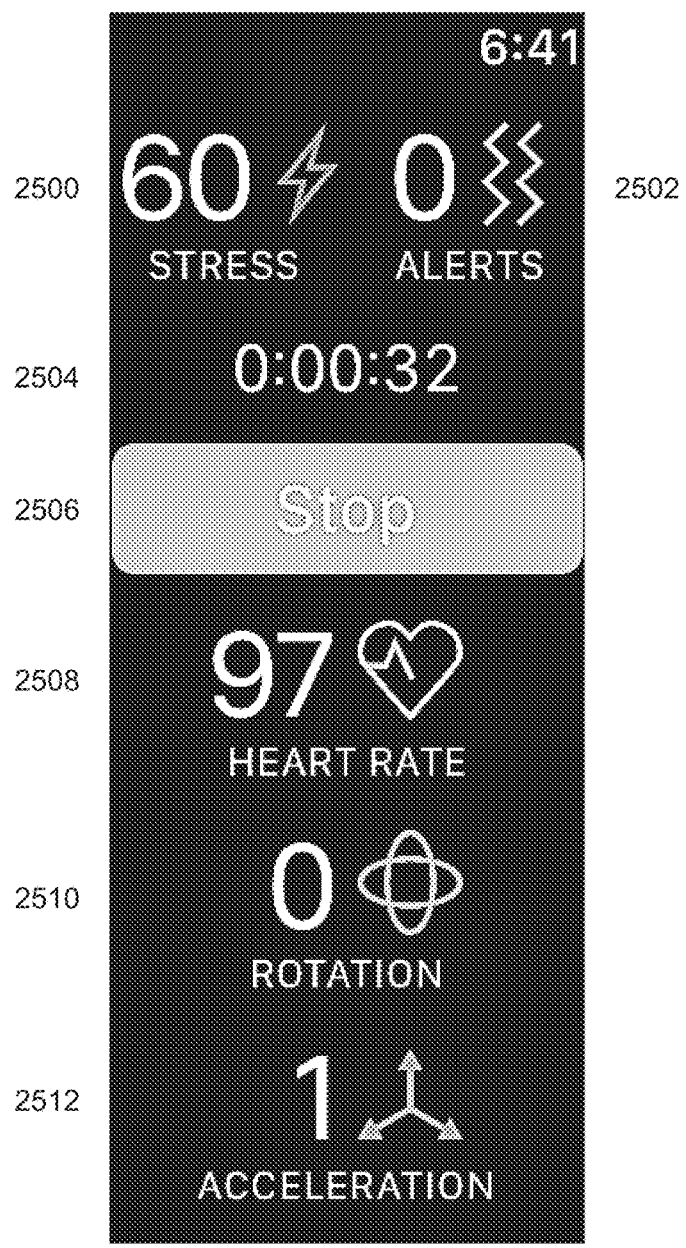
FIG. 26 is a screenshot of a monitoring page of a user interface for a wearable device of the present disclosure, according to one or more embodiments.

FIG. 26 is an example interface for stress monitoring in an embodiment of the present disclosure. The interface may include a stress level 2500, which may be a current stress level calculated in real time, or a most recently calculated stress level. The stress level 2500 may be an average stress level calculated over the past minute, for example. The interface may additionally include an alert count 2502 indicating how may alerts have been initiated in the present monitoring cycle, a duration 2504 indicating how long the present cycle has been monitoring stress, and/or a stop button 2506 to end the monitoring cycle. The interface may additionally provide current or most recent indications of sensed stress indicators. For example, the interface may provide a heart rate indicator 2508 indicating the user's current or most recently sensed heart rate, a rotation 2510 indicating the user's current or most recently sensed or calculated rotation, and an acceleration 2512 indicating the user's current or most recently sensed or calculated acceleration. A user may use this interface to, for example, review stress and sensor values or stop monitoring, as described above.

Figure 27:
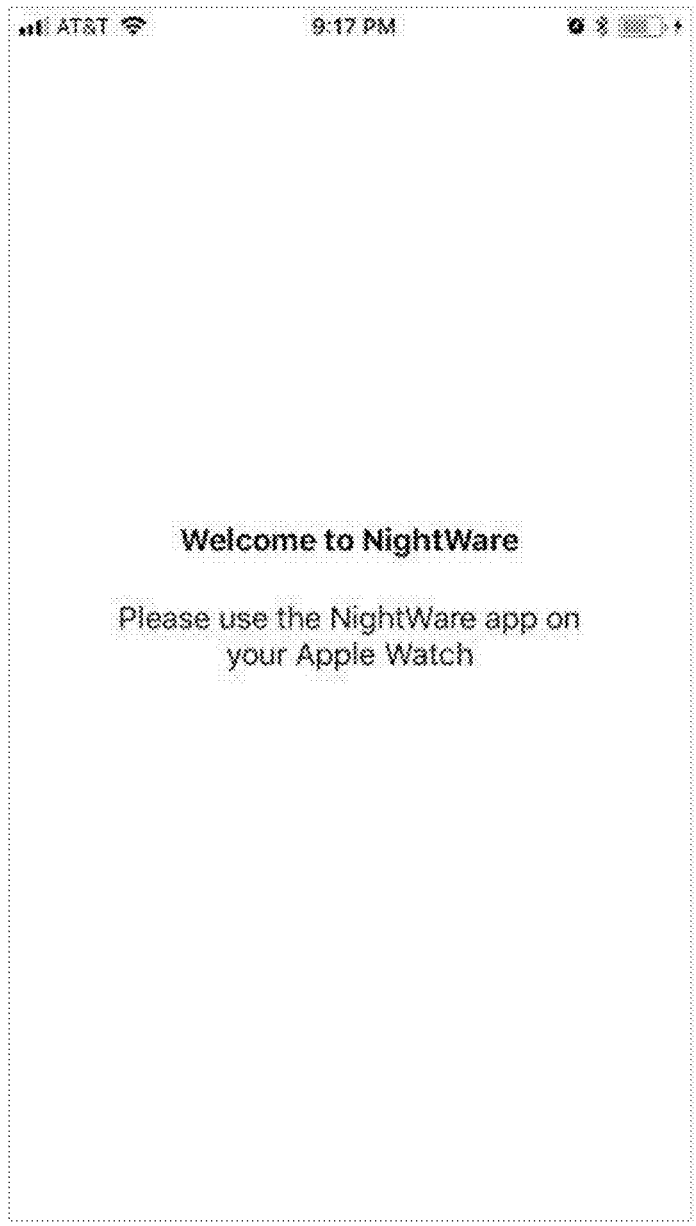
FIG. 27 is a screenshot of a user interface for a user device of the present disclosure, according to one or more embodiments.

As indicated above a user interface may be provided by a software application executed on a user device, such as a smartphone or other user device, in addition or alternative to a user interface provided via a wearable device. A user interface provided via a user device, such as a smartphone, may provide additional or alternative functionality to a user interface provided via a wearable device. FIG. 27 is an example interface in an embodiment of the present disclosure which may be provided via a smartphone or other user device. The interface may include one or more of a title 2600 and instructions 2602. This interface may integrate with an interface provided via a wearable device.

Figure 28:
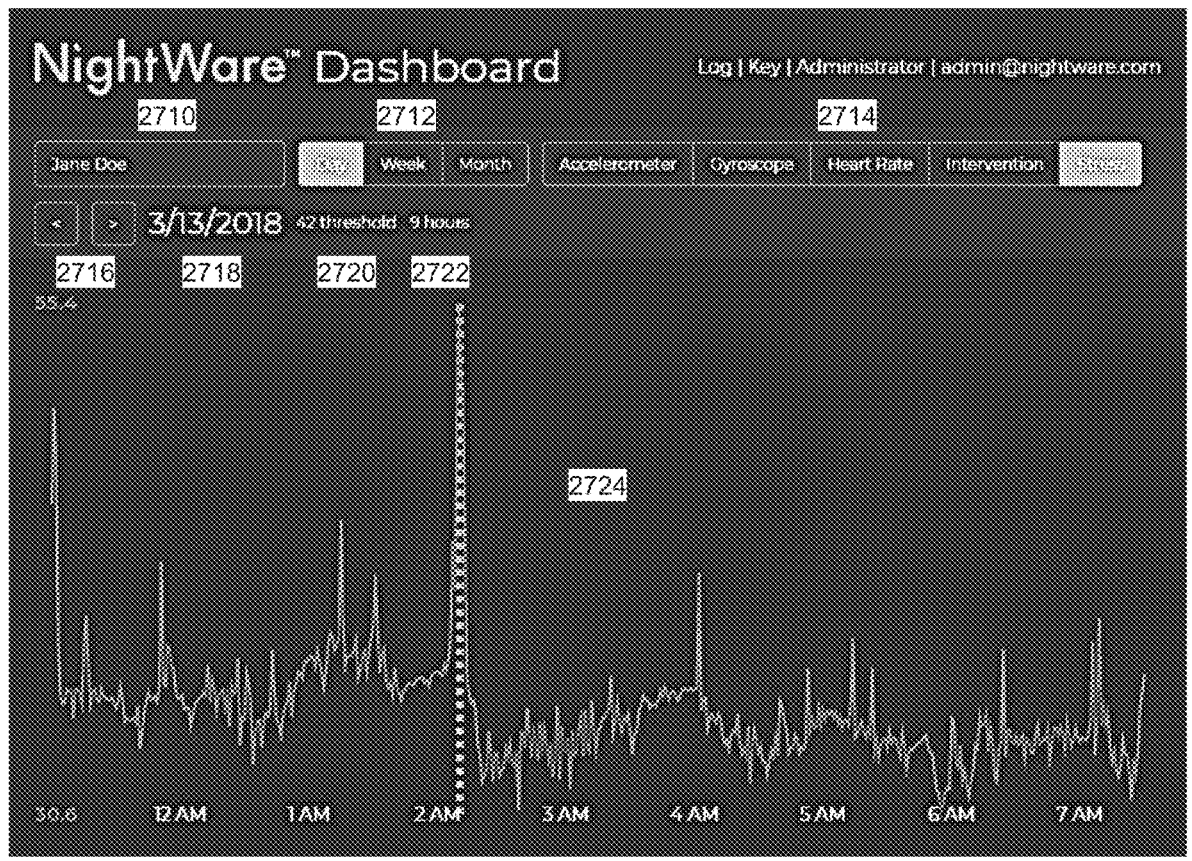
FIG. 28 is a screenshot of a dashboard page of a user interface of the present disclosure showing a user's stress level for a day, according to one or more embodiments.
Figure 29:
FIG. 29 is a screenshot of a dashboard page of a user interface of the present disclosure showing a user's stress level for a week, according to one or more embodiments.

FIGS. 28-29 provide additional views of an example user interface that may be provided via a user device, such as a smartphone, or via another user device or computing device.

FIG. 28 is an example dashboard interface in an embodiment of the present disclosure. The interface may include one or more of a title 2700, log link 2702, key link 2704, a user role 2706, and a user email 2708. The interface may additionally include a person selector 2710, by which a user may select among multiple individuals who may use the application for monitoring. The interface may provide a chart 2724 showing sensed or calculated stress data for the user over a specified duration. A duration selector 2712 may allow a user to change the duration over which the stress data is viewed, and a metric selector 2714 may allow the user to view different stress data. For example, the metric selector 2714 may include stress indicators such as accelerometer data, gyroscope data, and heart rate data. The metric selector may additionally allow a user to select intervention data to view interventions over a specified duration or stress data to view the user's calculated stress level over a specified duration. Previous and next buttons 2716 may provide for movement to different days, weeks, or months of data, and a date 2718 may display the particular date or date range for which data is displayed. A stress threshold 2720 may indicate the user's current stress threshold against which stress levels are compared to evaluate whether to intervene. A chart duration 2722 may indicate the amount of time currently displayed on the chart 2724. In this case, the chart 2724 shows a user's stress levels for a 9-hour period on a particular day (i.e., Mar. 13, 2018). A user may use this interface to, for example, review stress level, stress indicator, and intervention levels for a given user over a specified timeframe.

Figure 30:
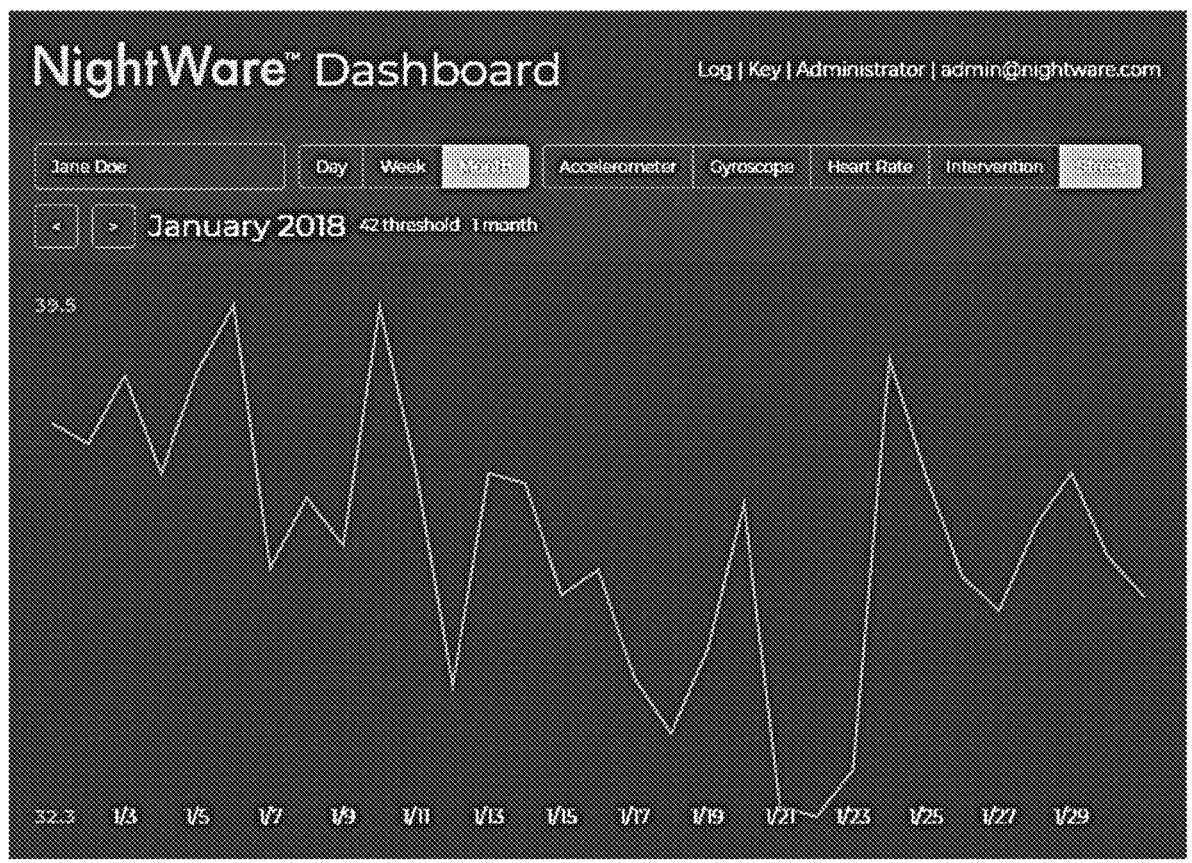
FIG. 30 is a screenshot of a dashboard page of a user interface of the present disclosure showing a user's stress level for a month, according to one or more embodiments.
Figure 31:
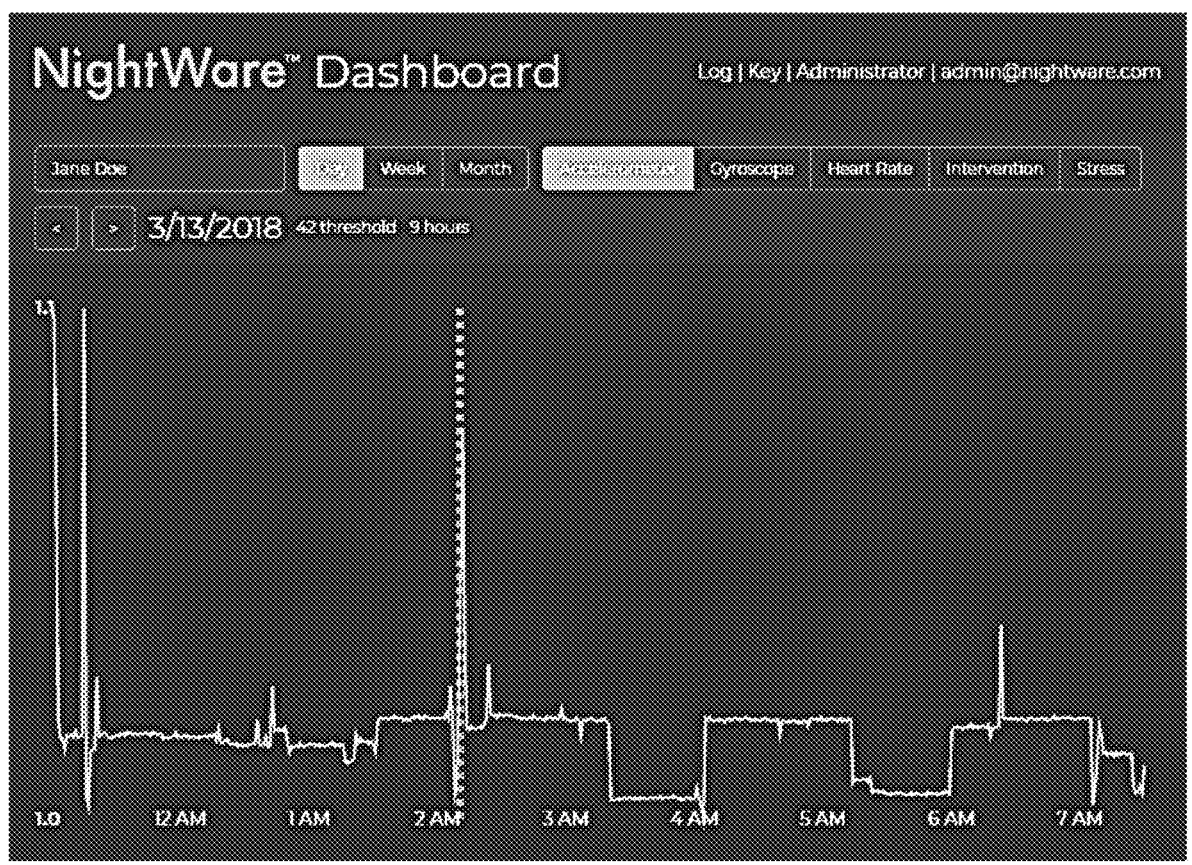
FIG. 31 is a screenshot of a dashboard page of a user interface of the present disclosure showing a user's sensed acceleration for a day, according to one or more embodiments.
Figure 32:
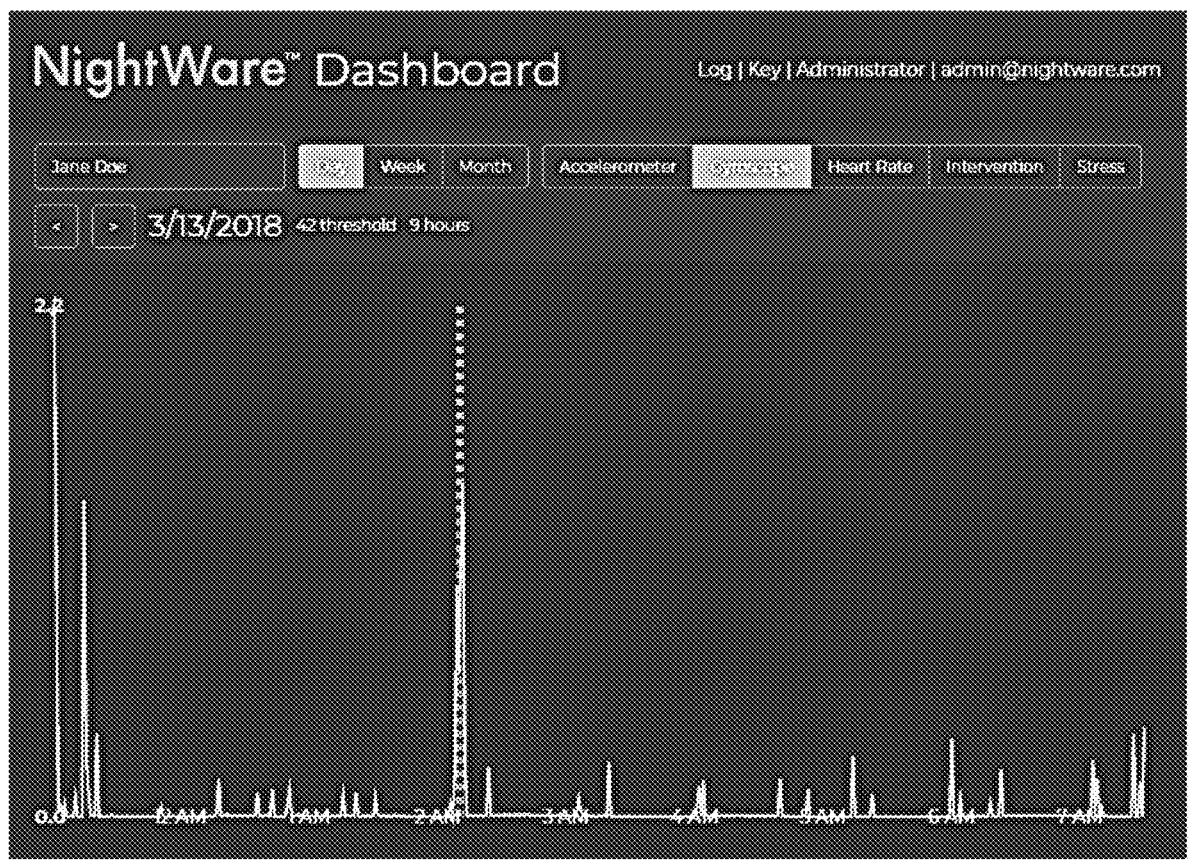
FIG. 32 is a screenshot of a dashboard page of a user interface of the present disclosure showing a user's sensed rotation for a day, according to one or more embodiments.
Figure 33:
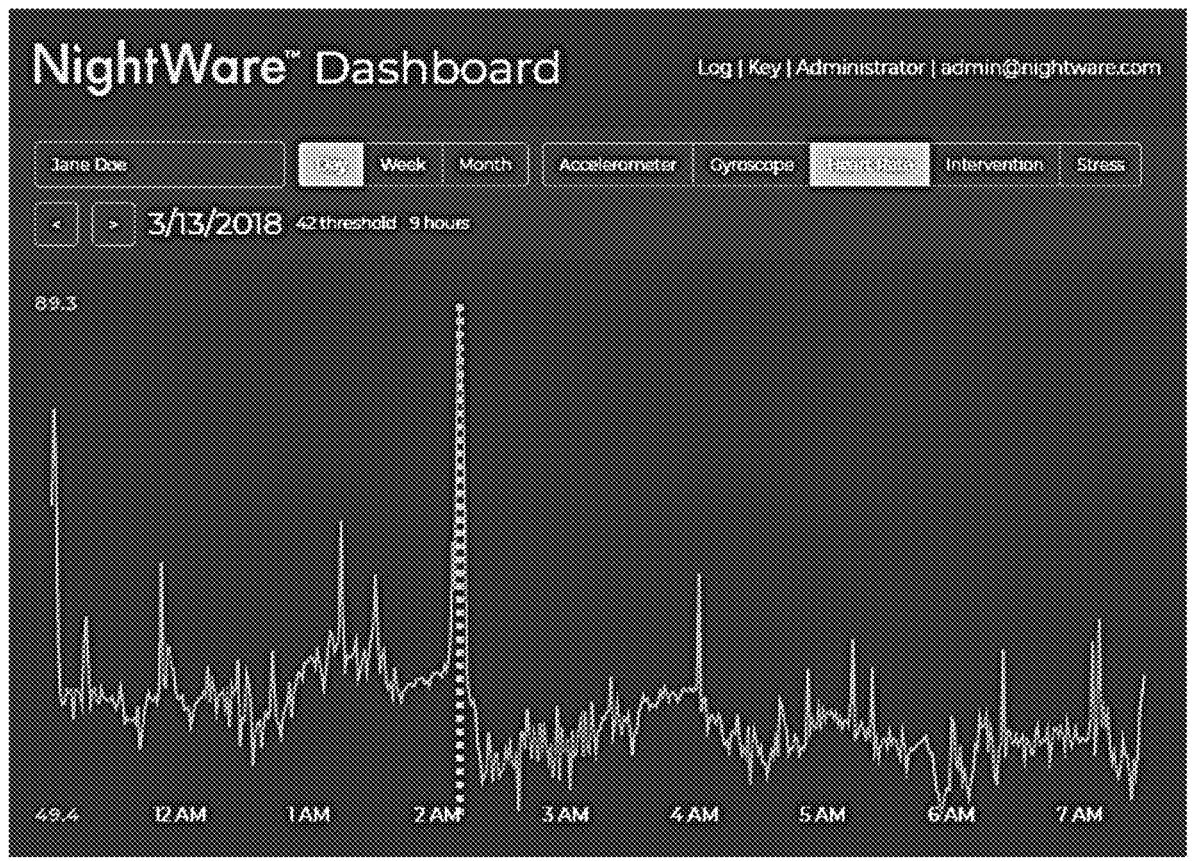
FIG. 33 is a screenshot of a dashboard page of a user interface of the present disclosure showing a user's sensed heart rate for a day, according to one or more embodiments.
Figure 34:
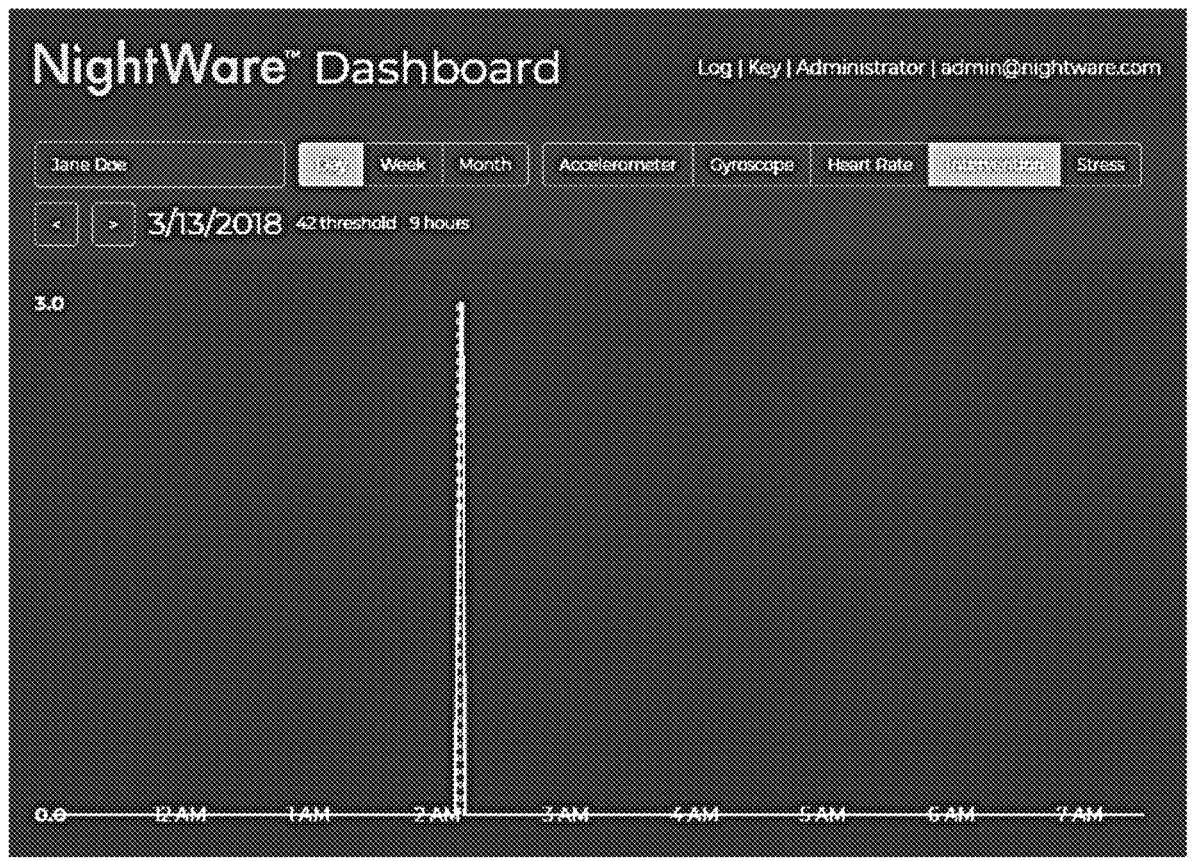
FIG. 34 is a screenshot of a dashboard page of a user interface of the present disclosure showing a user's intervention count for a day, according to one or more embodiments.

FIGS. 29-34 illustrate different example data views on the dashboard. In particular, FIG. 29 shows a user's calculated stress level displayed over a week. FIG. 30 shows a user's calculated stress level over a month. FIG. 31 shows the user's accelerometer stress indicator data, which may be a magnitude calculated from coordinate data for example, over a 9-hour period. FIG. 32 shows the user's gyroscope stress indicator data, which may be a magnitude calculated from coordinate data for example, over a 9-hour period. FIG. 33 shows the user's heart rate stress indicator data over a 9-hour period. FIG. 34 shows the user's interventions over a 9-hour period, and may display a number of interventions and/or an intensity or level of each intervention. It may be appreciated with reference to FIGS. 28 and 31-34 that the user may have experienced a stress episode on Mar. 13, 2018, shortly after 2 AM. The stress indicators of FIGS. 31-33 show elevated acceleration, rotation, and hear rate readings, respectively. The stress level of FIG. 28 shows a stress level rising to 55.4 shortly after 2 AM as well, which is above the user's indicated stress threshold 2720 of 42. Moreover, FIG. 34 illustrates that three interventions were initiated shortly after 2 AM on the same day. It may further be appreciated that FIGS. 28 and 31-34 demonstrate that the user's stress indicators and stress levels decreased after the interventions.

Figure 35:
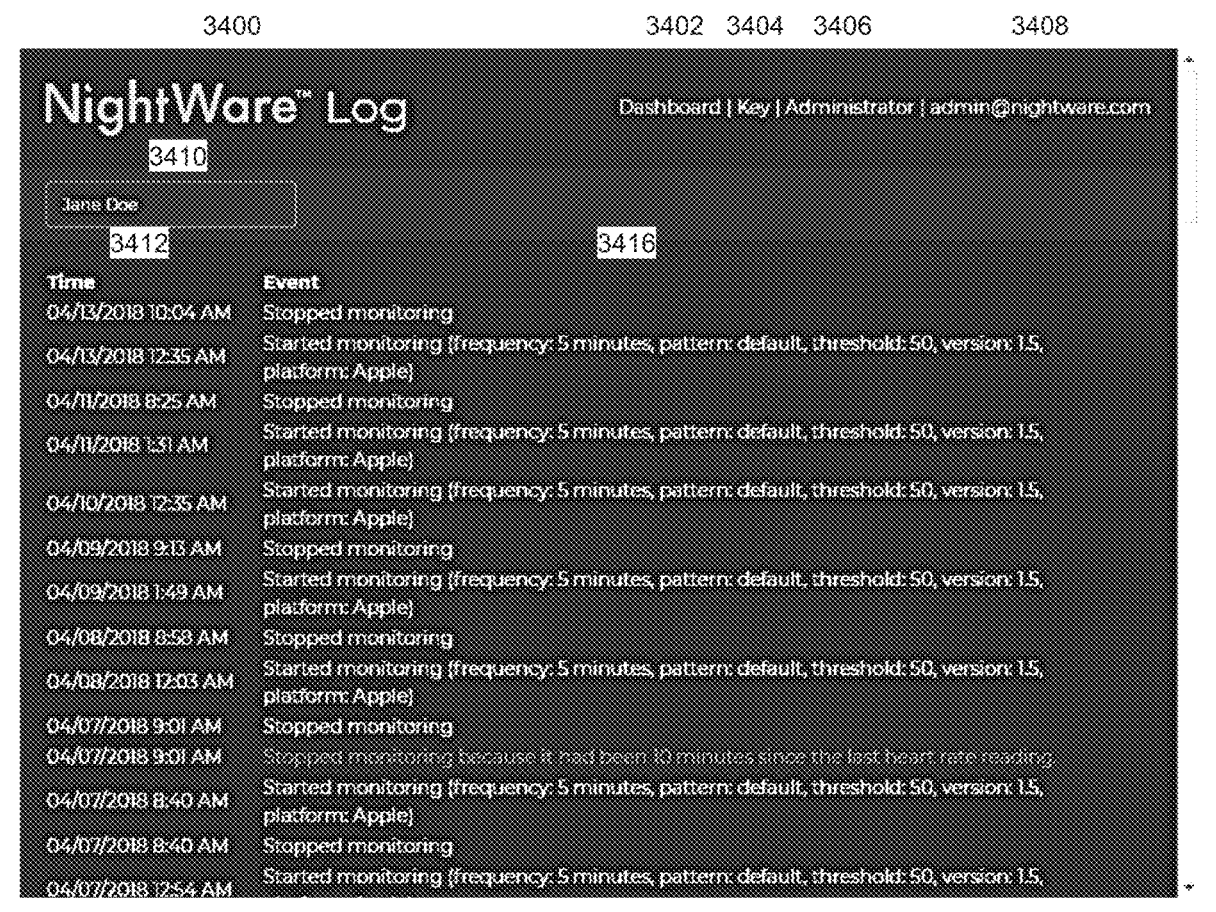

FIG. 35 is an example log interface in an embodiment of the present disclosure. The interface may include one or more of a title 3400, dashboard link 3402, key link 3404, user role 3406, user email 3408, person selector 3410, date/time column 3412, and event column 3416. A user may use this interface to, for example, review a user's start and stop times, any errors that occurred, and/or other logged events.

As indicated above, in some embodiments, a user may receive a monitoring summary or event summary. The summary may be sent to the user automatically at the end of a monitoring session, or at the end of a day, week, or month, for example. In other embodiments, the user may request a summary. The summary may be sent to the user via an email message in some embodiments. However, in other embodiments, the summary may be sent via a text message, push notification, popup window, and/or other suitable communication type. FIG. 36 shows an example daily summary email in an embodiment of the present disclosure. The summary may include one or more of a name column 3500, start column 3502, end column 3504, duration column 3506, interventions column 3508, minimum stress column 3510, average stress column 3512, maximum stress column 3514, and dashboard link 3516 to open the dashboard interface. A monitoring summary or event summary may be sent, automatically or manually, to an individual user whose stress was monitored and/or to other individuals or users. For example, a summary may be sent, automatically or manually, to a doctor or other healthcare professional or to a caretaker or family member. The summary may include monitoring data for more than one individual. For example, a healthcare professional may receive a monitoring summary or event summary with monitoring data related to a plurality of individuals whose stress data was monitored. In some embodiments, a user may opt to share her or his monitoring data. For example, a user may choose to share, or otherwise send, monitoring data for the user to a caretaker or healthcare professional. For example, the user may opt to have a summary email automatically sent to a caretaker with a daily summary of monitoring activity.

Figure 37:
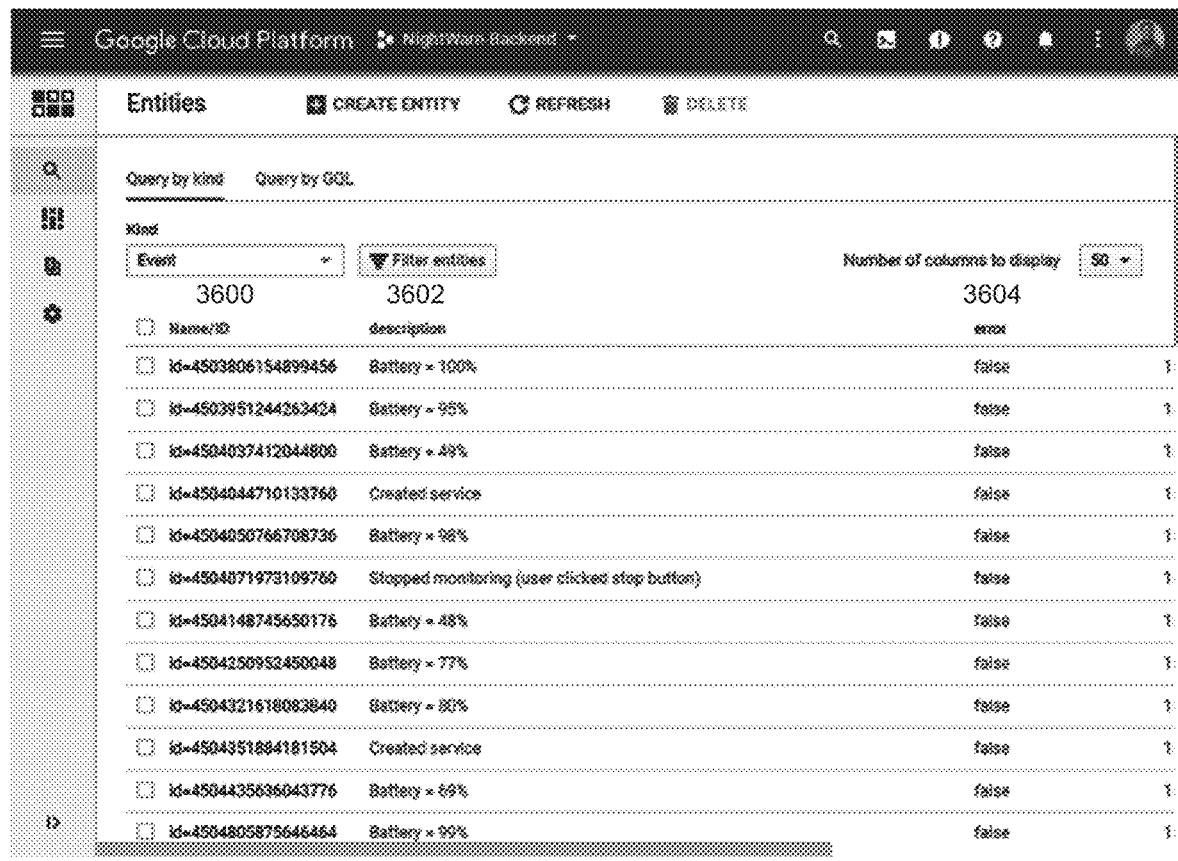
FIG. 37 is a screenshot of an events datastore accessible from a database of the present disclosure, according to one or more embodiments.
Figure 38:
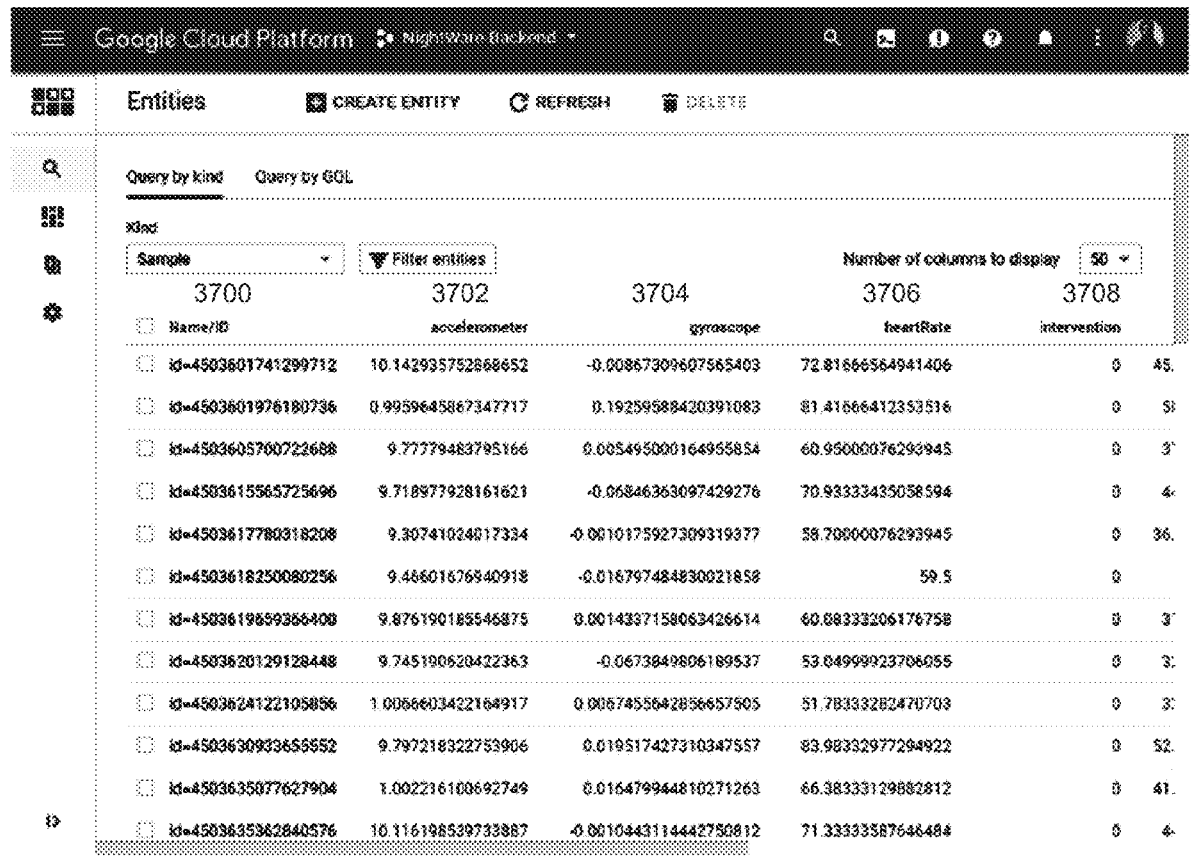
FIG. 38 is a screenshot of a samples datastore accessible from a database of the present disclosure, according to one or more embodiments.
Figure 39:
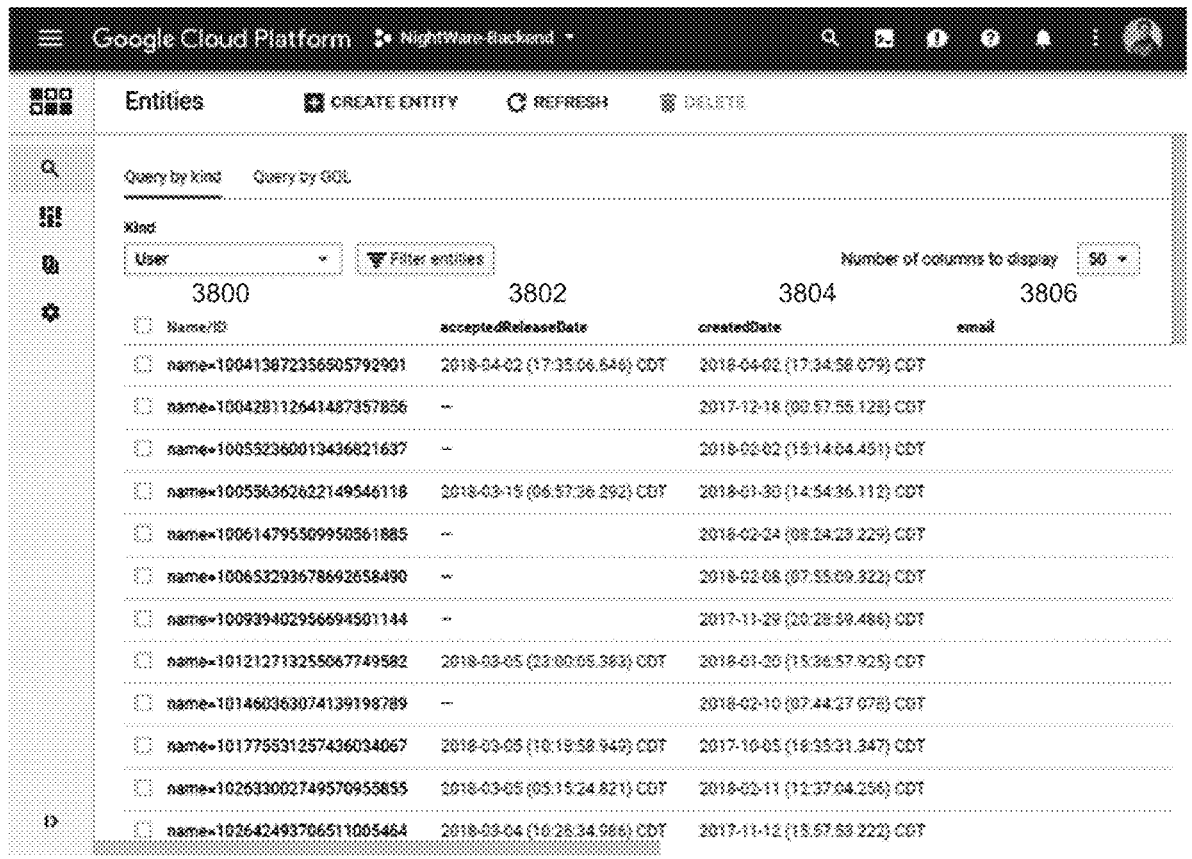
FIG. 39 is a screenshot of a users datastore accessible from a database of the present disclosure, according to one or more embodiments.

FIGS. 37-39 provide some examples of datastores that may be stored in a database of the present disclosure. For example, an event datastore may include information related to monitoring events for one or more users. A sample datastore may include raw sensor data collected for one or more users during one or more monitoring sessions. A user datastore may include information related to one or more users, such as information related to the users' acceptance of legal release terms and conditions. Such datastores may be available to individual users in some embodiments. Additionally or alternatively, datastores may be available to administrative users with administrative access rights to the database.

FIG. 37 is an example screenshot of an event datastore in an embodiment of the present disclosure. The event datastore may be or include a listing of monitoring events for one or more monitoring sessions and for one or more users stored in a database. The event datastore may be accessible via a user interface on a wearable device or user device. The event datastore may include one or more of an identifier column 3600, description column 3602, error column 3604, timestamp column, and user identifier column. A user may have the option to send or share her or his event data to a healthcare professional, caretaker, or other individual.

FIG. 38 is an example screenshot of a sample datastore in an embodiment of the present disclosure. The sample datastore may include a record of sample data (i.e., stress indicator data collected from one or more sensors during a monitoring session) for a user. The sample datastore may include one or more of an identifier column 3700, accelerometer column 3702, gyroscope column 3704, heart rate column 3706, intervention column 3708, stress column, timestamp column, and user identifier column. It is to be appreciated that where additional or alternative sensors are used to monitor stress indicators, additional columns for such stress indicators may be provided. A user may have the option to send or share her or his sample data to a healthcare professional, caretaker, or other individual.

FIG. 39 is an example screenshot of a user datastore in an embodiment of the present disclosure. The user datastore may include information related to one or more users, such as an indication of if and when each user has accepted the legal terms and conditions for use of the systems and methods described herein and/or personal, contact, or identifying information about the users. The user datastore may include one or more of an identifier column 3800, accepted release date column 3802, created date column 3804, email column 3806, key column, level column, name column, nickname column, and patients column.

Figure 40:
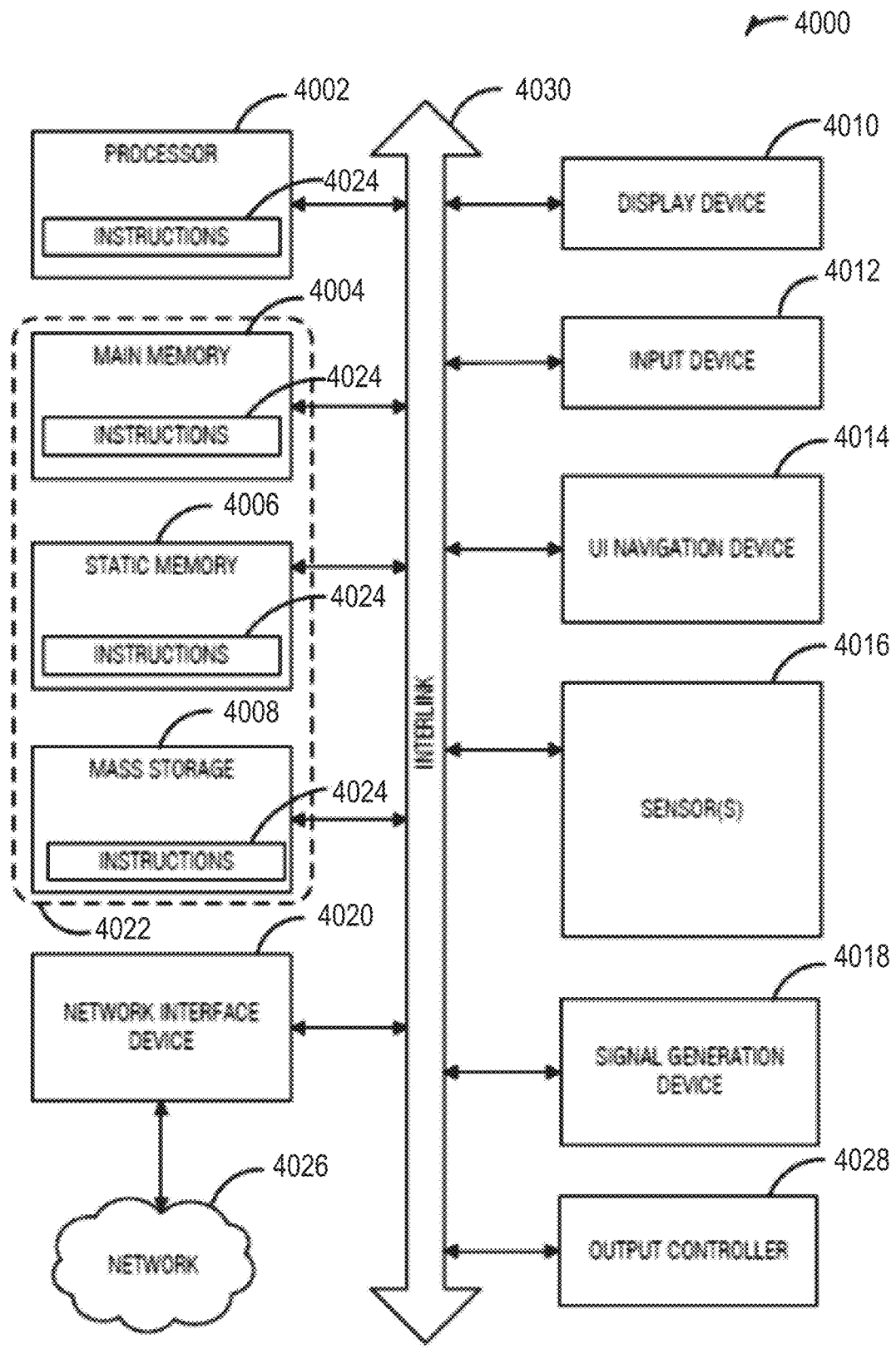
FIG. 40 a diagram of a system of the present disclosure, according to one or more embodiments.

FIG. 40 illustrates a block diagram of an example machine 4000 (such as the wearable device 100, personal device 102, computing device 104, or any other user device or combination of user devices described herein) upon which any one or more of the techniques (e.g., methods) discussed herein can perform. Examples, as described herein, can include, or can operate by, logic or a number of components or mechanisms in the machine 4000.

In some embodiments, the machine 4000 can operate as a standalone device or can be connected (e.g., networked) to other machines. In a networked deployment, the machine 4000 can operate in the capacity of a server machine, a client machine, or both in server-client network environments. In some examples, the machine 4000 can act as a peer machine in peer-to-peer (P2P) (or other distributed) network environment. The machine 4000 can be a personal computer (PC), a tablet PC, a set-top box (STB), a personal digital assistant (PDA), a mobile telephone, a smartphone, a personal fitness tracker, a smartwatch or other wearable device, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

The machine (e.g., computer system) 4000 can include a hardware processor 4002 (e.g., a central processing unit (CPU), a graphics processing unit (GPU), a hardware processor core, or any combination thereof), a main memory 4004, a static memory (e.g., memory or storage for firmware, microcode, a basic-input-output (BIOS), unified extensible firmware interface (UEFI), etc.) 4006, and mass storage 4008 (e.g., hard drives, tape drives, flash storage, or other block devices) some or all of which can communicate with each other via an interlink (e.g., bus) 4030. The machine 4000 can further include a display unit 4010, an alphanumeric input device 4012 (e.g., a keyboard), and a user interface (UI) navigation device 4014 (e.g., a mouse). In some examples, the display unit 4010, input device 4012 and UI navigation device 4014 can be a touch screen display. The machine 4000 can additionally include a storage device (e.g., drive unit) 4008, a signal generation device 4018 (e.g., a speaker), a network interface device 4020, and one or more sensors 4016, such as a global positioning system (GPS) sensor, compass, accelerometer, or other sensor. The machine 4000 can include an output controller 4028, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

Registers of the processor 4002, the main memory 4004, the static memory 4006, or the mass storage 4008 can be, or include, a machine readable medium 4022 on which is stored one or more sets of data structures or instructions 4024 (e.g., software) embodying or utilized by any one or more of the techniques or functions described herein. The instructions 4024 can also reside, completely or at least partially, within any of registers of the processor 4002, the main memory 4004, the static memory 4006, or the mass storage 4008 during execution thereof by the machine 4000. In some examples, one or any combination of the hardware processor 4002, the main memory 4004, the static memory 4006, or the mass storage 4008 can constitute the machine readable media 4022. While the machine readable medium 4022 is illustrated as a single medium, the term "machine readable medium" can include a single medium or multiple media (e.g., a centralized or distributed database, and/or associated caches and servers) configured to store the one or more instructions 4024.

The term "machine readable medium" can include any medium that is capable of storing, encoding, or carrying instructions for execution by the machine 4000 and that cause the machine 4000 to perform any one or more of the techniques of the present disclosure, or that is capable of storing, encoding or carrying data structures used by or associated with such instructions. Non-limiting machine readable medium examples can include solid-state memories, optical media, magnetic media, and signals (e.g., radio frequency signals, other photon based signals, sound signals, etc.). In some examples, a non-transitory machine readable medium comprises a machine readable medium with a plurality of particles having invariant (e.g., rest) mass, and thus are compositions of matter. Accordingly, non-transitory machine-readable media are machine readable media that do not include transitory propagating signals. Specific examples of non-transitory machine readable media can include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

In some examples, information stored or otherwise provided on the machine readable medium 4022 can be representative of the instructions 4024, such as instructions 4024 themselves or a format from which the instructions 4024 can be derived. This format from which the instructions 4024 can be derived can include source code, encoded instructions (e.g., in compressed or encrypted form), packaged instructions (e.g., split into multiple packages), or the like. The information representative of the instructions 4024 in the machine readable medium 4022 can be processed by processing circuitry into the instructions to implement any of the operations discussed herein. For example, deriving the instructions 4024 from the information (e.g., processing by the processing circuitry) can include: compiling (e.g., from source code, object code, etc.), interpreting, loading, organizing (e.g., dynamically or statically linking), encoding, decoding, encrypting, unencrypting, packaging, unpackaging, or otherwise manipulating the information into the instructions 4024.

In some examples, the derivation of the instructions 4024 can include assembly, compilation, or interpretation of the information (e.g., by the processing circuitry) to create the instructions 4024 from some intermediate or preprocessed format provided by the machine readable medium 4022. The information, when provided in multiple parts, can be combined, unpacked, and modified to create the instructions 4024. For example, the information can be in multiple compressed source code packages (or object code, or binary executable code, etc.) on one or several remote servers. The source code packages can be encrypted when in transit over a network and decrypted, uncompressed, assembled (e.g., linked) if necessary, and compiled or interpreted (e.g., into a library, stand-alone executable etc.) at a local machine, and executed by the local machine.

The instructions 4024 can be further transmitted or received over a communications network 4026 using a transmission medium via the network interface device 4020 utilizing any one of a number of transfer protocols (e.g., frame relay, internet protocol (IP), transmission control protocol (TCP), user datagram protocol (UDP), hypertext transfer protocol (HTTP), etc.). Example communication networks can include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, IEEE 802.16 family of standards known as WiMax®), IEEE 802.15.4 family of standards, peer-to-peer (P2P) networks, among others. In some examples, the network interface device 4020 can include one or more physical jacks (e.g., Ethernet, coaxial, or phone jacks) or one or more antennas to connect to the communications network 4026. In some examples, the network interface device 4020 can include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 4000, and includes digital or analog communications signals or other intangible medium to facilitate communication of such software. A transmission medium is a machine readable medium.

As will be appreciated by one of skill in the art, the various embodiments of the present disclosure may be embodied as a method (including, for example, a computer-implemented process, a business process, and/or any other process), apparatus (including, for example, a system, machine, device, computer program product, and/or the like), or a combination of the foregoing. Accordingly, embodiments of the present disclosure may take the form of an entirely hardware embodiment, an entirely software embodiment (including firmware, middleware, microcode, hardware description languages, etc.), or an embodiment combining software and hardware aspects. Furthermore, embodiments of the present disclosure may take the form of a computer program product on a computer-readable medium or computer-readable storage medium, having computer-executable program code embodied in the medium, that define processes or methods described herein. A processor or processors may perform the necessary tasks defined by the computer-executable program code. Computer-executable program code for carrying out operations of embodiments of the present disclosure may be written in an object oriented, scripted or unscripted programming language such as Java, Perl, PHP, Visual Basic, Smalltalk, C++, or the like. However, the computer program code for carrying out operations of embodiments of the present disclosure may also be written in conventional procedural programming languages, such as the C programming language or similar programming languages. A code segment may represent a procedure, a function, a subprogram, a program, a routine, a subroutine, a module, an object, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

Various embodiments of the present disclosure may be described herein with reference to flowchart illustrations and/or block diagrams of methods, apparatus (systems), and computer program products. It is understood that each block of the flowchart illustrations and/or block diagrams, and/or combinations of blocks in the flowchart illustrations and/or block diagrams, can be implemented by computer-executable program code portions. These computer-executable program code portions may be provided to a processor of a general purpose computer, special purpose computer, or other programmable data processing apparatus to produce a particular machine, such that the code portions, which execute via the processor of the computer or other programmable data processing apparatus, create mechanisms for implementing the functions/acts specified in the flowchart and/or block diagram block or blocks. Alternatively, computer program implemented steps or acts may be combined with operator or human implemented steps or acts in order to carry out an embodiment of the invention.

Additionally, although a flowchart or block diagram may illustrate a method as comprising sequential steps or a process as having a particular order of operations, many of the steps or operations in the flowchart(s) or block diagram(s) illustrated herein can be performed in parallel or concurrently, and the flowchart(s) or block diagram(s) should be read in the context of the various embodiments of the present disclosure. In addition, the order of the method steps or process operations illustrated in a flowchart or block diagram may be rearranged for some embodiments. Similarly, a method or process illustrated in a flow chart or block diagram could have additional steps or operations not included therein or fewer steps or operations than those shown. Moreover, a method step may correspond to a method, a function, a procedure, a subroutine, a subprogram, etc.

As used herein, the terms "substantially" or "generally" refer to the complete or nearly complete extent or degree of an action, characteristic, property, state, structure, item, or result. For example, an object that is "substantially" or "generally" enclosed would mean that the object is either completely enclosed or nearly completely enclosed. The exact allowable degree of deviation from absolute completeness may in some cases depend on the specific context. However, generally speaking, the nearness of completion will be so as to have generally the same overall result as if absolute and total completion were obtained. The use of "substantially" or "generally" is equally applicable when used in a negative connotation to refer to the complete or near complete lack of an action, characteristic, property, state, structure, item, or result. For example, an element, combination, embodiment, or composition that is "substantially free of" or "generally free of" an element may still actually contain such element as long as there is generally no significant effect thereof.

To aid the Patent Office and any readers of any patent issued on this application in interpreting the claims appended hereto, applicants wish to note that they do not intend any of the appended claims or claim elements to invoke 35 U.S.C. § 112(f) unless the words "means for" or "step for" are explicitly used in the particular claim.

Additionally, as used herein and unless otherwise clear from the context, the phrase "at least one of [X] and [Y]," or "at least one of [X] or [Y]," where X and Y are different components that may be included in an embodiment of the present disclosure, means that the embodiment could include component X without component Y, the embodiment could include the component Y without component X, or the embodiment could include both components X and Y. Similarly, when used with respect to three or more components, such as "at least one of [X], [Y], and [Z]," or "at least one of [X], [Y], or [Z]," the phrase means that the embodiment could include any one of the three or more components, any combination or sub-combination of any of the components, or all of the components.

In the foregoing description various embodiments of the present disclosure have been presented for the purpose of illustration and description. They are not intended to be exhaustive or to limit the invention to the precise form disclosed. Obvious modifications or variations are possible in light of the above teachings. The various embodiments were chosen and described to provide the best illustration of the principals of the disclosure and their practical application, and to enable one of ordinary skill in the art to utilize the various embodiments with various modifications as are suited to the particular use contemplated. All such modifications and variations are within the scope of the present disclosure as determined by the appended claims when interpreted in accordance with the breadth they are fairly, legally, and equitably entitled.

What is claimed is:

1. A method for monitoring a user's stress and for interrupting a stress episode, the method comprising:
   determining a stress level threshold for the user, the stress level threshold indicating a stress level at which the user is experiencing a stress episode;
   receiving a plurality of sensor readings from a wearable device worn by the user and determining a stress level of the user based on the plurality of sensor readings;
   comparing the stress level to the stress level threshold; and
   if the stress level exceeds the stress level threshold, initiating an intervention protocol at the wearable device to alert the user and interrupt the stress episode, the intervention protocol comprising haptic feedback at the wearable device;
   wherein the stress level threshold is learned upon receiving at least a certain amount of sensor readings from the wearable device and is based on a specified percentile of historical stress levels for the user.

2. The method of claim 1, further comprising evaluating data sensed by the wearable device to determine the user is at rest, wherein the step of determining the stress level of the user is initiated after determining the user is at rest.

3. The method of claim 1, further comprising:
   determining an amount of time since a most recent intervention protocol; and
   comparing the amount of time since the most recent intervention protocol to a stored minimum frequency;
   wherein initiating an intervention protocol to interrupt the stress episode is performed only if the amount of time since the most recent intervention protocol meets or exceeds the minimum frequency.

4. The method of claim 1, wherein determining a stress level threshold for the user comprises determining a plurality of stress level thresholds for the user, wherein each stress level threshold is learned upon receiving at least the certain amount of sensor readings from the wearable device and each stress level threshold is based on a different specified percentile of the historical stress levels for the user.

5. The method of claim 4, wherein:
   comparing the stress level to the stress level threshold comprises comparing the stress level to one or more of the stress level thresholds; and
   if the stress level exceeds at least one of the one or more stress level thresholds, initiating an intervention protocol corresponding to at least one of the one or more stress level thresholds exceeded.

6. The method of claim 5, wherein each stress level threshold corresponds to a different intervention protocol.

7. The method of claim 1, further comprising:
   determining a plurality of subsequent stress levels of the user, each of the subsequent stress levels based on a corresponding plurality of sensor readings; and
   continuing the intervention protocol until the subsequent stress levels indicate a certain reduction in the user's stress.

8. The method of claim 1, wherein the plurality of sensor readings comprise readings from a plurality of sensors of the wearable device.

9. A system for monitoring a user's stress and for interrupting a stress episode, the system comprising:
   a wearable device, configured to be worn by the user; and
   computer-executable instructions, that when executed by at least one processor at least one of which is provided in the wearable device, cause the at least one processor to:
   determine a stress level threshold for the user, the stress level threshold indicating a stress level at which the user is experiencing a stress episode;
   receive a plurality of sensor readings from the wearable device and determine a stress level of the user based on the plurality of sensor readings;
   compare the stress level to the stress level threshold; and
   if the stress level exceeds the stress level threshold, initiate an intervention protocol at the wearable device to alert the user and interrupt the stress episode, the intervention protocol comprising haptic feedback at the wearable device;
   wherein the stress level threshold is learned upon receiving at least a certain amount of sensor readings from the wearable device and is based on a specified percentile of historical stress levels for the user.

10. The system of claim 9, wherein the computer-executable instructions cause the at least one processor to evaluate data sensed by the wearable device to determine the user is at rest, and to determine the stress level of the user after determining the user is at rest.

11. The system of claim 9, wherein the computer-executable instructions cause the at least one processor to:
    determine an amount of time since a most recent intervention protocol;
    compare the amount of time since the most recent intervention protocol to a stored minimum frequency; and
    initiate the intervention protocol to interrupt the stress episode only if the stress level exceeds the stress level threshold and the amount of time since the most recent intervention protocol meets or exceeds the minimum frequency.

12. The system of claim 9, wherein determining a stress level threshold for the user comprises determining a plurality of stress level thresholds for the user, wherein each stress level threshold is learned upon receiving at least the certain amount of sensor readings from the wearable device and each stress level threshold is based on a different specified percentile of the historical stress levels for the user.

13. The system of claim 12, wherein:
    comparing the stress level to the stress level threshold comprises comparing the stress level to one or more of the stress level thresholds; and
    if the stress level exceeds at least one of the one or more stress level thresholds, the computer-executable instructions cause the at least one processor to initiate an intervention protocol corresponding to at least one of the one or more stress level thresholds exceeded.

14. The system of claim 13, wherein each stress level threshold corresponds to a different intervention protocol.

15. The system of claim 9, wherein the computer-executable instructions cause the at least one processor to:
    determine a plurality of subsequent stress levels of the user, each of the subsequent stress levels based on a corresponding plurality of sensor readings; and
    continue the intervention protocol until the subsequent stress levels indicate a certain reduction in the user's stress.

16. The system of claim 9, wherein the plurality of sensor readings comprise readings from a plurality of sensors of the wearable device.

17. A non-transitory computer readable storage medium comprising executable instructions, that when executed by at least one processor, cause the at least one processor to:
    receive a sensor reading from a wearable device, configured to be worn by a user, and determine to intervene a stress episode of the user based on the sensor reading;

determine an amount of time since a most recent intervention protocol;

compare the amount of time since the most recent intervention protocol to a stored minimum frequency; and in response to determining to intervene, and only if the amount of time since the most recent intervention protocol meets or exceeds the minimum frequency, initiate an intervention protocol at the wearable device to alert the user and interrupt the stress episode, the intervention protocol comprising haptic feedback at the wearable device.

18. The non-transitory computer readable storage medium of claim 17, wherein the executable instructions cause the at least one processor to receive a plurality of sensor readings from the wearable device and determine to intervene based on the plurality of sensor readings.

19. The non-transitory computer readable storage medium of claim 17, wherein the executable instructions cause the at least one processor to evaluate data sensed by the wearable device to determine the user is at rest, and to determine to intervene after determining the user is at rest.

* * * * *